United States Patent
Masaki et al.

[11] Patent Number: 5,574,030
[45] Date of Patent: Nov. 12, 1996

[54] N-AMINOALKYL-SUBSTITUTED NITROGEN-CONTAINING FIVE MEMBERED HETEROCYCLIC COMPOUNDS

[75] Inventors: Mitsuo Masaki, Chiba; Norihisa Miyake, Saitama; Atsushi Tendo, Saitama; Hiromitsu Takeda, Saitama; Michiko Ishida, Saitama; Haruhiko Shinozaki, Saitama, all of Japan

[73] Assignee: Nippon Chemiphar Co., Ltd., Tokyo, Japan

[21] Appl. No.: 91,219

[22] Filed: Jul. 13, 1993

Related U.S. Application Data

[63] Continuation-in-part of Ser. No. 55,969, Apr. 30, 1993, abandoned.

[30] Foreign Application Priority Data

Jul. 14, 1992 [JP] Japan .................. 4-209713

[51] Int. Cl.$^6$ .................. C07D 233/32; C07D 233/42; A61K 31/505; A61K 31/54
[52] U.S. Cl. .................. 514/212; 540/604; 544/60; 544/133; 544/137; 544/139; 546/209; 546/210; 548/183; 548/184; 548/227; 548/230; 514/227.8; 514/235.8; 514/236.8; 514/235.5; 514/326; 514/369; 514/398
[58] Field of Search .................. 540/604; 544/60, 544/133, 137, 139; 546/209, 210; 548/183, 184, 227, 230; 514/212, 227.8, 235.8, 236.8, 235.5, 326, 369, 398

[56] References Cited

U.S. PATENT DOCUMENTS 3,873,560  3/1975  Mcmenim .................. 260/306 FT

OTHER PUBLICATIONS

Dickinson et al., "The Analyst" 96(1138) 235–243 (1971).

Primary Examiner—Matthew V. Grumbling
Attorney, Agent, or Firm—McAulay Fisher Nissen Goldberg & Kiel, LLP

[57] ABSTRACT

Disclosed are new alkylenediamine derivatives of the following formula which are effective for treatment of dysuria are disclosed:

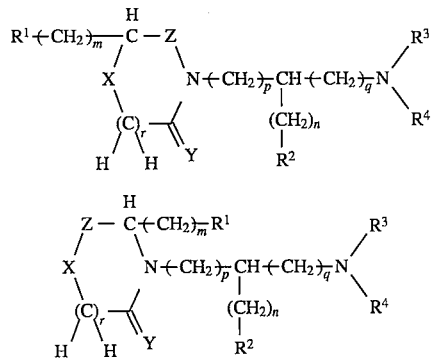

wherein $R^1$ is hydrogen, alkyl, or a substituted or unsubstituted phenyl, naphthyl or aromatic heterocyclic group; $R^2$ is a substituted or unsubstituted phenyl, naphthyl or aromatic heterocyclic group; $R^3$ and $R^4$ represent hydrogen, alkyl, aralkyl or aryl; or $R^3$ and $R^4$ are combined to form one of substituted or unsubstituted 5- to 7-membered heterocyclic groups; X is oxygen, sulfur or imino; Y is oxygen or sulfur; Z is —CH$_2$—, —CO— or —CS—; m is an integer of 0–4; n is an integer of 0–4; r is 0 or 1; and p and q represent an integer of 0–5 provided that p plus q is 1–5.

18 Claims, 2 Drawing Sheets

(a)

(b) ClCO₂R (c)

(d)

(e)

(f)

(g)

(i) H₂NCONH₂

N-AMINOALKYL-SUBSTITUTED NITROGEN-CONTAINING FIVE MEMBERED HETEROCYCLIC COMPOUNDS

This is a continuation-in-part of patent application Ser. No. 08/055,969, filed Apr. 30, 1993, now abandoned.

BACKGROUND OF THE INVENTION

1. Field of the Invention

The present invention relates to a novel alkylenediamine derivative, a process for the preparation of said compound, and a remedy for dysuria containing said novel alkylenediamine derivative or a pharmaceutically acceptable salt of the compound as active ingredient.

2. Description of Prior art

Hitherto, it has been known that flavoxate hydrochloride and oxybutynine hydrochloride are able to inhibit the urinary contraction, and therefore they have been used as remedy for dysuria. However, since they directly give peripheral action to the bladder, side effects on other organs such as digestive organs are sometimes observed.

Recently, Japanese Patent Provisional Publication No. 1(1989)-319418 discloses that the following 1,3-oxazolidin-2-one derivatives and their pharmaceutically acceptable salts are effective for treatment of dysuria:

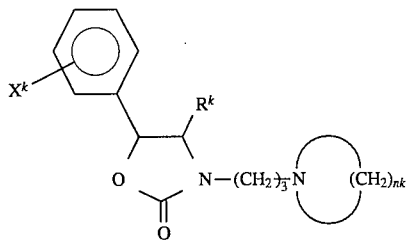

wherein $R^k$ represents a straight chain or branched chain alkyl group of 3–8 carbon atoms; $X^k$ represents hydrogen atom, a halogen atom, a lower alkyl group or a lower alkoxy group; and nk is 4, 5 or 6.

SUMMARY OF THE INVENTION

An object of the present invention is to provide a new alkylenediamine derivative which can inhibit the urinating contraction occurring under high intracystic pressure, and a new remedy for dysuria.

The present invention resides in an alkylenediamine derivative represented by the formula (1) or (2):

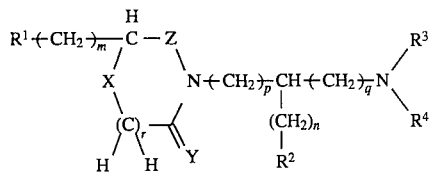

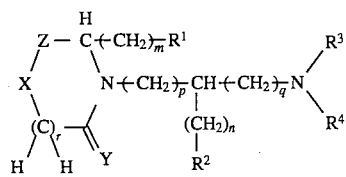

wherein $R^1$ represents a hydrogen atom, an alkyl group, or a phenyl, naphthyl or aromatic heterocyclic group which may have the same or different 1 to 5 substituent groups selected from those consisting of alkyl groups, halogen atoms, haloalkyl groups, hydroxyl group, alkoxyl groups, aryloxy groups, aralkyloxy groups, nitro group, amino group, cyano group, alkylamino groups, aralkylamino groups, arylamino groups, acylamino groups, carboxyl group, alkoxycarbonyl groups, aralkyloxycarbonyl groups, aryloxycarbonyl groups, carbamoyl group, sulfo group, alkoxysulfonyl groups, aralkyloxysulfonyl groups, aryloxysulfonyl groups, sulfonamide group and 1H-tetrazol-5-yl group; $R^2$ represents a phenyl, naphthyl or aromatic heterocyclic group which may have the same or different 1 to 5 substituent groups selected from those consisting of alkyl groups, halogen atoms, haloalkyl groups, hydroxyl group, alkoxyl groups, aryloxy groups, aralkyloxy groups, nitro group, amino group, cyano group, alkylamino groups, aralkylamino groups, arylamino groups, acylamino groups, carboxyl group, alkoxycarbonyl groups, aralkyloxycarbonyl groups, aryloxycarbonyl groups, carbamoyl group, sulfo group, alkoxysulfonyl groups, aralkyloxysulfonyl groups, aryloxysulfonyl groups, sulfonamide group and 1H-tetrazol-5-yl group; each of $R^3$ and $R^4$ independently represents hydrogen atom, an alkyl group, an aralkyl group or an aryl group, or $R^3$ and $R^4$ are combined to form one of 5- to 7-membered cyclic groups which may contain oxygen atom, sulfur atom or nitrogen atom besides the nitrogen atom connected to both of $R^3$ and $R^4$ and which may have the same or different 1 to 5 substituent groups selected from those consisting of alkyl groups, aralkyl groups, phenyl group, hydroxyl group, alkoxyl groups, carboxyl group, alkoxycarbonyl groups, aralkyloxycarbonyl groups, aryloxycarbonyl groups, acyl groups, and carbamoyl group; X represents oxygen atom, sulfur atom or imino group; Y represents oxygen atom or sulfur atom; Z represents —$CH_2$—, —CO— or —CS—; m is an integer of 0–4; n is an integer of 0–4; r is 0 or 1; and each of p and q independently represents an integer of 0–5 provided that p plus q is 1–5.

One of representative compounds of the formula (1) is represented by the formula (3):

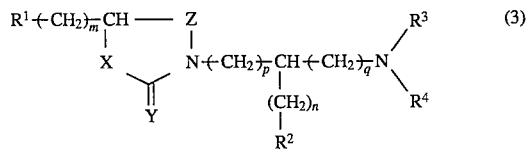

wherein each of $R^1$ and $R^2$ independently represents a phenyl, naphthyl or aromatic heterocyclic group which may have the same or different 1 to 5 substituent groups selected from those consisting of alkyl groups, halogen atoms, haloalkyl groups, hydroxyl group, alkoxyl groups, aryloxy groups, aralkyloxy groups, nitro group, amino group, alkylamino groups, aralkylamino groups, arylamino groups, acylamino groups, carboxyl group, alkoxycarbonyl groups, aralkyloxycarbonyl groups, aryloxycarbonyl groups, carbamoyl group, sulfo group, alkoxysulfonyl groups, aralkyloxysulfonyl groups, aryloxysulfonyl groups, sulfonamide group and 1H-tetrazol-5-yl group; each of $R^3$ and $R^4$ independently represents hydrogen atom, an alkyl group, an aralkyl group or an aryl group, or $R^3$ and $R^4$ are combined to form one of 5- to 7-membered cyclic groups which may contain oxygen atom, sulfur atom or nitrogen atom besides the nitrogen atom connected to both of $R^3$ and $R^4$ and which may have the same or different 1 to 5 substituent groups selected from those consisting of alkyl groups, aralkyl groups, phenyl group, hydroxyl group, alkoxyl groups, carboxyl group, alkoxycarbonyl groups, aralkyloxycarbonyl groups, aryloxycarbonyl groups and carbamoyl group; X represents oxygen atom, sulfur atom or imino group; Y represents oxygen atom or sulfur atom; Z represents —CH$_2$—, —CO— or —CS—; m is an integer of 0–4; n is an integer of 0–4; and each of p and q independently represents an integer of 0–5 provided that p plus q is 1–5.

Another representative compound of the formula (1) is represented by the formula (4)

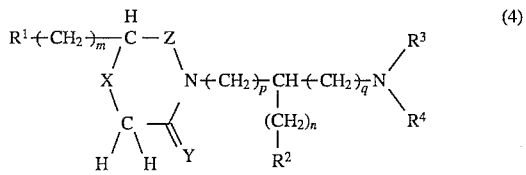

wherein each of R$^1$, R$^2$ R$^3$, R$^4$, X, Y, Z, m, n, p, and q has the same meansing as defined for the formulas (1) and (2).

One of representative compounds of the formula (2) is represented by the formula (5)

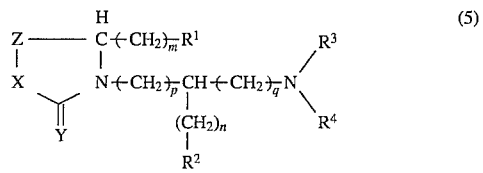

wherein each of R$^1$, R$^2$ R$^3$, R$^4$, X, Y, Z, m, n, p, and q has the same meansing as defined for the formulas (1) and (2).

Another representative compound of the formula (2) is represented by the formula (6)

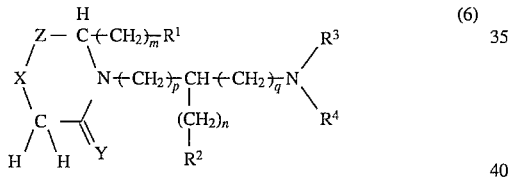

wherein each of R$^1$, R$^2$ R$^3$, R$^4$, X, Y, Z, m, n, p, and q has the same meansing as defined for the formulas (1) and (2).

The alkylenediamine derivatives of the formulas (1), (2), (3), (4), (5) and (6), and their pharmaceutically acceptable salts can inhibit the urinary contraction occurring under high intracystic pressure by acting not on the peripheral nerves system but on the central nerves system, and therefore they can be used as excellent remedy for dysuria, which can cure dysuria, incontinence of urine and morbid uresiesthesia caused by diseases such as nervous dysuria, chromic prostatitis and chromic cystitis.

The alkylenediamine derivatives of the invention having the formulas (1) and (2) can be prepared by a process wherein a compound represented by the formula (7) or (8):

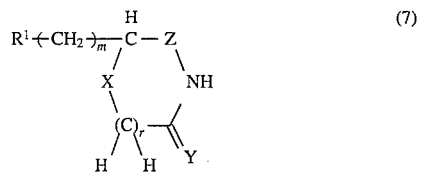

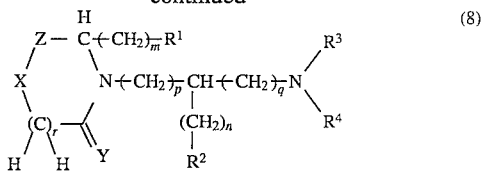

wherein each of R$^1$, X, Y, Z, m and r has the same meaning as defined above is caused to react with a compound represented by the formula (9):

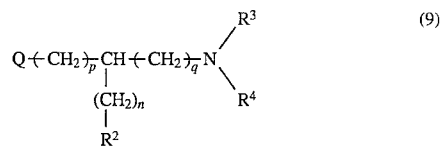

wherein each of R$^2$, R$^3$, R$^4$, n, p and q has the same meaning as defined above, and Q represents a releasable group such as a halogen atom, tosyloxy group or mesyloxy group.

The alkylenediamine derivative of the invention also can be prepared by process wherein a compound represented by the formula (10) or (11):

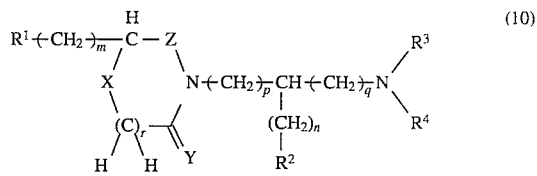

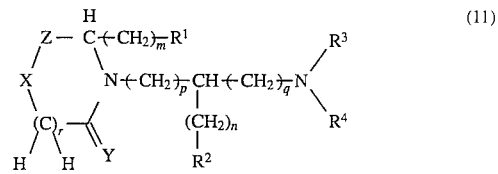

wherein each of R$^1$, R$^2$, X, Y, Z, Q, m, n, p, q and r has the same meaning as defined above is caused to react with a compound represented by the formula (12):

wherein each of R$^3$ and R$^4$ has the same meaning as defined above.

The alkylenediamine derivative of the invention having the formula (3) can be prepared by a process wherein a compound represented by the formula (13):

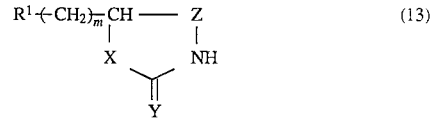

wherein each of R$^1$, X, Y, Z and m has the same meaning as defined above is caused to react with a compound represented by the formula (9):

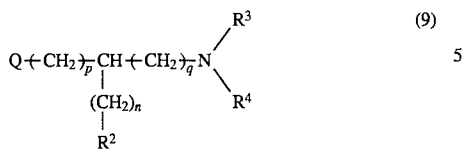

wherein each of $R^2$, $R^3$, $R^4$, n, p and q has the same meaning as defined above, and O represents a releasable group.

The alkylenediamine derivative of the invention having the formula (3) also can be prepared by process wherein a compound represented by the formula (14):

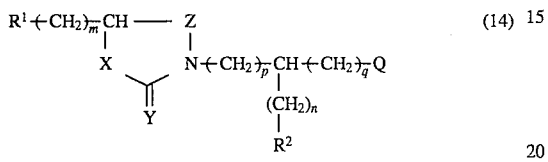

wherein each of $R^1$, $R^2$, X, Y, Z, 0, m, n, p and q has the same meaning as defined above
is caused to react with a compound represented by the formula (12):

wherein each of $R^3$ and $R^4$ has the same meaning as defined above.

The alkylenediamine derivative of the above formula (3) according to the invention wherein X, Y and Z are oxygen atom, oxygen atom and —$CH_2$—, respectively, can be prepared by a process wherein a compound represented by the formula (15):

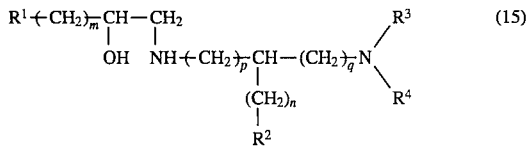

wherein each of $R^1$, $R^2$, $R^3$, $R^4$, m, n, p and q has the same meaning as defined above
is caused to react with a reagent which is used for synthesizing 2-oxazolidone from 1,2-aminoalcohol.

The alkylenediamine derivative of the above formula (3) according to the invention wherein X, Y and Z are oxygen atom, sulfur atom and —$CH_2$—, respectively, can be prepared by a process wherein the compound of the above formula (15) is caused to react with carbon disulfide and an alkyl chloroformate, phosgene or dialkyl carbonate.

The alkylenediamine derivative of the above formula (3) according to the invention wherein X, Y and Z are oxygen atom, oxygen atom and —$CH_2$—, respectively, can be prepared by a process wherein a compound represented by the formula (16):

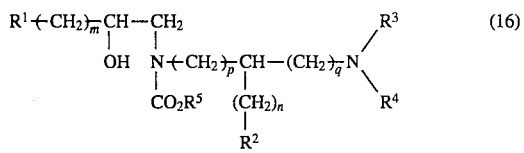

wherein each of $R^1$, $R^2$, $R^3$, $R^4$, m, n, p and q has the same meansing as defined above, and $R^5$ represents an alkyl group
is subjected to ring-closing reaction under heating.

The alkylenediamine derivative of the formula (3) according to the invention wherein X, Y and Z are oxygen atom, oxygen atom and —$CH_2$—, respectively, can be prepared by a process wherein a compound represented by the formula (17):

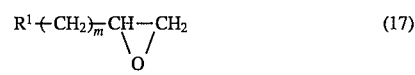

wherein each of $R^1$ and m has the same meansing as defined above.
is caused to react with a compound represented by the formula (18):

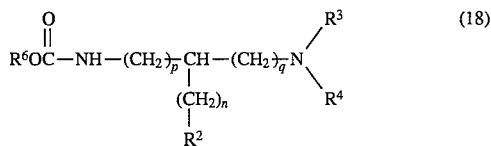

wherein each of $R^2$, $R^3$, $R^4$, n, p and q has the same meaning as defined above, and $R^6$ represents an alkyl group.

The alkylenediamine derivatives of the above formulas (1), (2), (3), (4), (5) and (6) according to the invention can be prepared in the form of pharmaceutically acceptable salts.

The alkylenediamine derivatives of the above formulas as well as their pharmaceutically acceptable salts according to the invention can be effectively employable for treatment of dysuria.

DETAILED DESCRIPTION OF INVENTION

Figure 1:
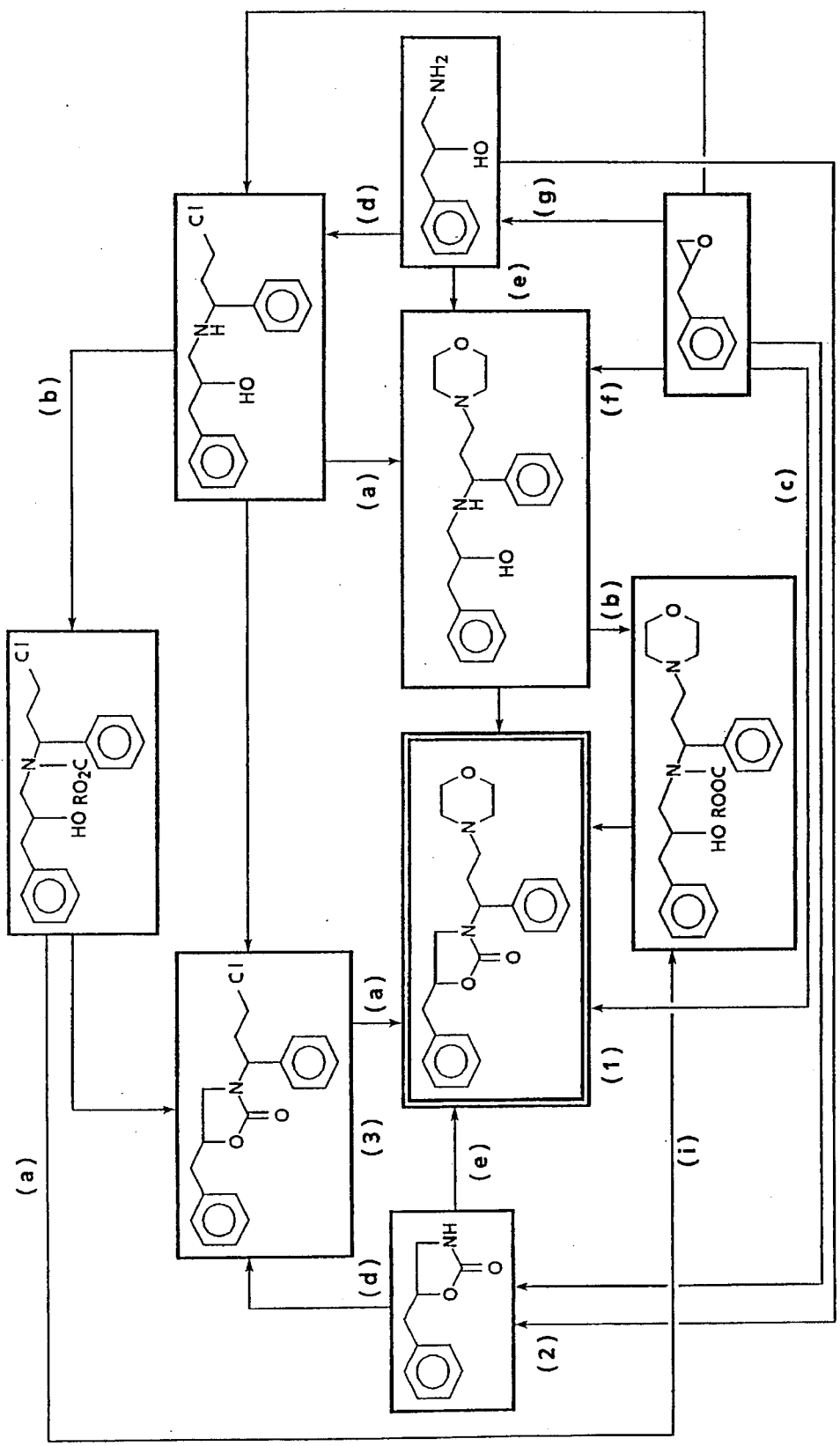
FIG. 1 shows various routes to prepare the compound of Example 1, namely, 5-benzyl-3-(3-morpholino-1-phenyl-propyl)-1,3-oxazolidin-2-one.

The alkylenediamine derivatives of the invention represented by the above formulas (1) and (2) are further described below.

In the formulas (1) and (2), $R^1$ represents a hydrogen atom, an alkyl group (such as alkyl having 1 to 6 carbon atoms, e.g., methyl, ethyl, propyl, isopropyl, butyl, isobutyl or pentyl), or a phenyl, naphthyl or aromatic heterocyclic group (preferred examples of such group include phenyl group, naphthyl group, furan ring, thiophene ring, pyridine ring, quinoline ring and indole ring) which may have the same or different 1 to 5 substituent groups; and $R^2$ represents a phenyl, naphthyl or aromatic heterocyclic group (preferred examples of such group include phenyl group, naphthyl group, furan ring, thiophene ring, pyridine ring, quinoline ring and indole ring) which may have the same or different 1 to 5 substituent groups.

In the formula (3), particularly, the group represented by $R^1$ or $R^2$ is phenyl group, naphthyl group or an aromatic heterocyclic group (preferred examples of such group include phenyl group, naphthyl group, furan ring, thiophene ring (that is, thienyl), pyridine ring, quinoline ring and indole ring), all of which may have the same or different 1 to 5 substituent groups.

Preferred is phenyl or thienyl group which may have the same or different 1 to 5 substituent groups, and more preferred is phenyl group having no substituent group or phenyl group substituted with 1 to 5 alkyl groups, alkoxyl groups, halogen atoms or haloalkyl groups; and further, particularly preferred is phenyl having no substituent.

With respect to the above substituent groups; a preferred example of the alkyl group is an alkyl group having 1–8 carbon atoms (e.g., methyl, ethyl, propyl, isopropyl, butyl, isobutyl, pentyl, hexyl, heptyl, octyl, etc.,); preferred examples of the halogen atom include fluorine, chlorine and bromine; preferred examples of the haloalkyl group include trifluoromethyl, chloromethyl and fluoromethyl; a preferred example of the alkoxyl group is an alkoxyl group having 1–8 carbon atoms such as methoxy, ethoxy or propoxy; preferred examples of the aryloxyl group include phenoxy and parachlorophenoxy; preferred examples of the aralkyloxyl group include benzyloxy; a preferred example of the alkylamino group is an alkylamino group having 1–8 carbon atoms such as methylamino, dimethylamino, ethylamino, propylamino and isobutylamino; preferred examples of the aralkylamino group include benzylamino and (4-chlorophenyl)methylamino; preferred examples of the arylamino group include phenylamino and parachlorophenylamino; a preferred example of the acylamino group is an acylamino group having 1–8 carbon atoms such as acetylamino and propionylamino; preferred examples of the alkoxycarbonyl group include methoxycarbonyl, ethoxycarbonyl and propoxycarbonyl; preferred examples of the aralkyloxycarbonyl group include benzyloxycarbonyl; preferred examples of the aryloxycarbonyl group include phenoxycarbonyl; preferred examples of the alkoxysulfonyl group include methoxysulfonyl and ethoxysulfonyl; preferred examples of the aralkyloxysulfonyl group include benzyloxysulfonyl; and preferred examples of the aryloxysulfonyl group include phenoxysulfonyl.

The group represented by $R^3$ or $R^4$ in the formulas (1), (2), (3), (4), (5) and (6) is, preferably, an alkyl group. It is also preferred that $R^3$ and $R^4$ be combined to form one of 5- to 7-membered cyclic groups containing the nitrogen atom connected to both of $R^3$ and $R^4$. A preferred example of such alkyl group is an alkyl group having 1–8 carbon atoms (e.g., methyl, ethyl, propyl, isopropyl, butyl, isobutyl, etc.,); and preferred examples of the aralkyl group include benzyl, phenylethyl and phenylpropyl; and preferred examples of the aryl group include phenyl, pyridyl and naphthyl. The above-mentioned alkyl groups are particularly preferred. Preferred examples of the 5- to 7-membered cyclic groups in which $R^3$ and $R^4$ are combined to form together with the nitrogen atom connected to both of $R^3$ and $R^4$ are 5- to 7-membered cyclic groups which may contain an additional hetero-atom. Concrete examples of the preferred cyclic groups include morpholino, piperidino, homomorpholino, 1-pyrrolidyl, thiomorpholino, and 1-piperazinyl. These cyclic groups can have one or more (1 to 5) substituents such as alkyl of 1–5 carbon atoms, alkoxy of 1–5 carbon atoms, acyl group such as formyl, acetyl, propionyl, benzoyl, phthaloyl, and hydroxyl. It two or more substituents are attached, these substituents can be the same or different from each other. Unsubstituted morpholino is particularly preferred.

In the formulas (1) and (3), the ring structure represented by the formula (19):

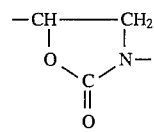 (19)

preferably is a structure represented by the following formula (20a), (20b), (20c) or (20d):

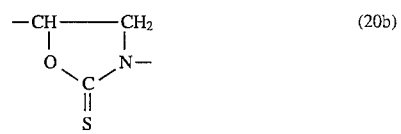 (20a)

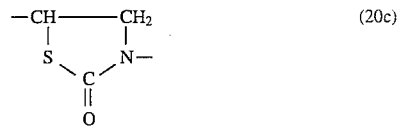 (20b)

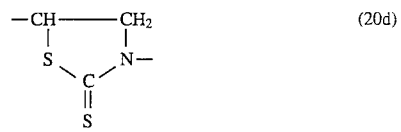 (20c)

 (20d)

The compound of the formula (20a) is particularly preferred.

In the formulas (1) to (6); m preferably is 0, 1 or 2, and particularly preferred is 1; n preferably is 0, 1 or 2, and particularly preferred is 0; p preferably is 0; and q preferably is 2.

Since the carbon atom connected to $R^1$—$(CH_2)_m$— and the carbon atom connected to $R^2$—$(CH_2)_n$— in the formulas (1) to (6) is an asymmetric carbon, the compound represented by the formulas (1) to (6) has two diastereomers and four optical isomers. However, any of a racemate, optical isomers and the mixture of the optical isomers are included in the invention.

Examples of the pharmaceutically acceptable salt of the alkylenediamine derivative represented by the formulas (1) to (6), include acid addition salts of inorganic acids (e.g., hydrochloric acid, sulfuric acid, hydrobromic acid and phosphoric acid) and organic acids (e.g., fumaric acid, acetic acid, propionic acid, citric acid, tartaric acid, maleic acid, malic acid, oxalic acid, methanesulfonic acid and paratoluenesulfonic acid).

The alkylenediamine derivative of the invention can be prepared by a process wherein a compound represented by the above formula (7) or (8) is caused to react with a compound represented by the above formula (9).

In this process, the compound represented by the formula (7) or (8) is caused to react with the compound represented by the formula (9) in an organic solvent such as acetone, methyl ethyl ketone, isobutyl methyl ketone or dimethylformamide in the presence of a carbonate such as potassium carbonate, sodium carbonate and cesium carbonate at a temperature between room temperature and the refluxing temperature for 2–50 hours to prepare the compound represented by the formula (1) or (2). The preferred amounts of the compound represented by the formula (9) and the carbonate are 1–2 mol and 2–8 mol, respectively, per 1 mol of the compound represented by the formula (7) or (8). It is also preferred that the compound represented by the formula (9) be used in the form of a stable hydrochloride.

The alkylenediamine derivative of the invention can be prepared by a process wherein a compound represented by the above formula (10) or (11) is caused to react with a compound represented by the above formula (12).

In this process, the compound represented by the formula (10) or (11) is caused to react with the compound represented by the formula (12) at 50°–150° C. for 1–7 hours to prepare the compound represented by the formula (1) or (2). This process is usually carried out using no solvent, but an inert solvent may be optionally used.

The alkylenediamine derivative of the formula (3) according to the invention wherein X, Y and Z are oxygen atom, oxygen atom, and —$CH_2$—, respectively, can be prepared by a process wherein a compound represented by the formula (15) is caused to react with a reagent which is used for synthesizing 2-oxazolidone from 1,2-amino-alcohol.

Examples of the employable reagents used for synthesizing 2-oxazolidone from 1,2-amino-alcohol in the process include phosgene, trichloromethylchloroformate, diethylcarbonate and urea. This process can be generally carried out in a mixed solvent of water and an organic solvent in the presence of a base.

The alkylenediamine derivative of the formula (3) according to the invention wherein X, Y and Z are oxygen atom, sulfur atom and —$CH_2$—, respectively, can be prepared by a process wherein a compound represented by the formula (15) is caused to react with carbon disulfide and an alkyl chloroformate.

In this process, the compound represented by the formula (15) can be caused to react with carbon disulfide and ethyl chloroformate in a mixed solvent such as dioxanecarbon tetrachloride in the presence of a base such as triethylamine to prepare the compound represented by the above formula (3) provided that X, Y and Z are oxygen atom, sulfur atom and —$CH_2$—, respectively.

The alkylenediamine derivative of the formula (3) according to the invention wherein X, Y, and Z are oxygen atom, oxygen atom and —$CH_2$—, respectively, can be prepared by a process wherein a compound represented by the formula (16) is subjected to ring-closing reaction under heating.

This process can be carried out by heating the compound of the formula (16) [which can be prepared, for example, by causing the compound of the formula (15) react with the compound of the formula: $ClCO_2R^5$] at the temperature between 50° C. and the refluxing temperature in an organic solvent such as toluene and xylene in the presence of a base such as sodium methoxide, sodium ethoxide and aluminum isopropoxide. In performing the process, it is preferred to remove the by-produced alcohol ($R^5OH$) together with the solvent.

The alkylenediamine derivative of the formula (3) of the invention wherein X, Y and Z are oxygen atom, oxygen atom and —$CH_2$—, respectively, can be prepared by a process wherein a compound of the above formula (17) is caused to react with a compound of the above formula (18).

In this process, the compound of the formula (17) and the compound of the formula (18) are heated to fuse or heated with stirring, in the presence of a catalyst, so as to cause reaction. Examples of the catalyst include bases such as triethylamine, quaternary ammonium halide, lithium n-butoxide, sodium hydroxide and lithium hydroxide; and Lewis acids such as zinc bromide, zinc chloride and iron chloride. This process is preferably carried out at 100°–150° C. for a few hours.

Figure 2:
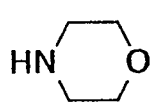
FIG. 2 shows the compounds represented by the small letters in FIG. 1.
Figure 2:
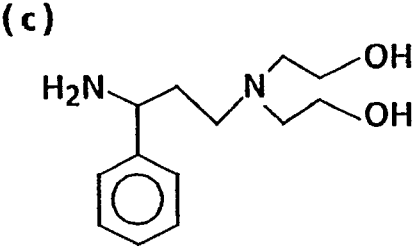
Figure 2:
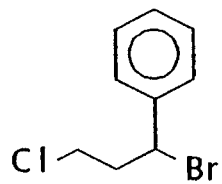
Figure 2:
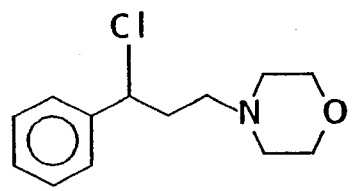
Figure 2:
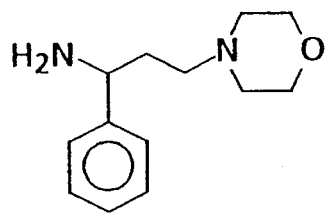
Figure 2:
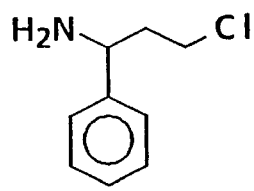

The alkylenediamine derivative of the invention can be prepared by any of the above-described various methods or by combination of well-known reactions. Various routes to synthesize 5-benzyl-3-(3-morpholino-1-phenylpropyl)-1,3-oxazolidin-2-one [Compound (1)], which is described in Example 1, are set forth in FIG. 1. In FIG. 1, the route to prepare Compound (1) from Compound (2) and Compound (e) corresponds to the first process, and the route to prepare Compound (1) from Compound (a) and Compound (3), which is derived from Compound (2), corresponds to the second process. Each of the small letters in FIG. 1 means the corresponding compound shown in FIG. 2.

The optical isomers of the alkylenediamine derivative of the invention can be obtained by syntheses using optical active intermediates or by the steps of separating four optical isomers into two diastereoisomers (each of which is a racemic mixture of the alkylenediamine derivative) by means of silica gel column chromatography and performing optical resolution of each diastereoisomer in the known manner. In the case that the compound of the formula (3) is synthesized by the reaction of the compound of the formula (17) and the compound of the formula (18), for example, the optical active compound of the formula (3) can be synthesized under the condition that both of the compounds of the formulae (17) and (18) are optical active. If only one of them is optical active, the optical active compound of the formula (3) can be obtained by the steps of separating diastereomers using ordinary silica gel column chromatography.

Representative examples of the alkylenediamine derivatives of the formula (3), which correspond to the alkylenediamine derivatives of the formula (1) wherein "r" is 0, are set forth in the following table, wherein "Ex. No" in the column for "Example" refers to the synthesis example number described hereinafter in the specification.

| $R^1$ | m | X | Y | Z | p | q | n | $R^2$ | $NR^3R^4$ | Example |
|---|---|---|---|---|---|---|---|---|---|---|
| Phenyl | 0 | O | O | $CH_2$ | 0 | 2 | 0 | phenyl | morpholino | Ex. 7 |
| 4-Methyl-phenyl | 0 | O | O | $CH_2$ | 0 | 2 | 0 | phenyl | morpholino | — |
| 4-Chloro-phenyl | 0 | O | O | $CH_2$ | 0 | 2 | 0 | phenyl | morpholino | — |
| 1-Naphthyl | 1 | O | O | $CH_2$ | 0 | 2 | 0 | phenyl | morpholino | Ex. 46 |
| 5-Bromo-S-furyl | 0 | O | O | $CH_2$ | 0 | 2 | 0 | phenyl | morpholino | — |
| 2-Thienyl | 0 | O | O | $CH_2$ | 0 | 2 | 0 | phenyl | morpholino | — |
| 2-Thienyl | 0 | O | O | $CH_2$ | 0 | 2 | 0 | 2-methyl-phenyl | morpholino | — |
| 4-Pyridyl | 0 | O | O | $CH_2$ | 0 | 2 | 0 | 2-methyl-phenyl | morpholino | — |
| 3-Indolyl | 0 | O | O | $CH_2$ | 0 | 2 | 0 | 2-methyl-phenyl | morpholino | — |

-continued

| R¹ | m | X | Y | Z | p | q | n | R² | NR³R⁴ | Example |
|---|---|---|---|---|---|---|---|---|---|---|
| Phenyl | 1 | O | O | CH₂ | 0 | 2 | 0 | phenyl | dimethyl-amino | — |
| Phenyl | 1 | O | O | CH₂ | 0 | 2 | 0 | phenyl | piperidino | — |
| Phenyl | 1 | O | O | CH₂ | 0 | 2 | 0 | phenyl | morpholino | Ex. 1 |
| Phenyl | 1 | O | O | CH₂ | 0 | 2 | 1 | phenyl | morpholino | — |
| Phenyl | 1 | O | O | CH₂ | 0 | 2 | 0 | phenyl | 2-methyl-morpholino | — |
| Phenyl | 1 | O | O | CH₂ | 0 | 2 | 0 | phenyl | 4-acetyl-1-piperazinyl | — |
| Phenyl | 1 | N | O | CH₂ | 0 | 2 | 0 | phenyl | morpholino | — |
| Phenyl | 1 | O | S | CH₂ | 0 | 2 | 0 | phenyl | morpholino | — |
| Phenyl | 1 | S | S | CS | 0 | 2 | 0 | phenyl | morpholino | — |
| Phenyl | 1 | O | O | CO | 0 | 2 | 0 | phenyl | morpholino | Ex. 12 |
| 2-Chloro-phenyl | 1 | O | O | CH₂ | 0 | 2 | 0 | phenyl | morpholino | Ex. 15 |
| 3-Chloro-phenyl | 1 | O | O | CH₂ | 0 | 2 | 0 | phenyl | morpholino | Ex. 31 |
| 4-Chloro-phenyl | 1 | O | O | CH₂ | 0 | 2 | 0 | phenyl | morpholino | Ex. 23 |
| 3,4-Dichloro-2-phenyl | 1 | O | O | CH₂ | 0 | 2 | 0 | phenyl | morpholino | — |
| 2-Bromo-phenyl | 1 | O | O | CH₂ | 0 | 2 | 0 | phenyl | morpholino | Ex. 13 |
| 2-Bromo-phenyl | 1 | O | O | CH₂ | 0 | 2 | 0 | phenyl | 1-pyrrolinyl | Ex. 29 |
| 2-Fluoro-phenyl | 1 | O | O | CH₂ | 0 | 2 | 0 | phenyl | morpholino | Ex. 48 |
| 2-Nitro-phenyl | 1 | O | O | CH₂ | 0 | 2 | 0 | phenyl | morpholino | — |
| 4-Trifluoromethyl-phenyl | 1 | O | O | CH₂ | 0 | 2 | 0 | phenyl | morpholino | — |
| 3-Methyl-phenyl | 1 | O | O | CH₂ | 0 | 2 | 0 | phenyl | morpholino | Ex. 38 |
| 4-Methoxy-phenyl | 1 | O | O | CH₂ | 0 | 2 | 0 | phenyl | morpholino | Ex. 54 |
| 4-Methoxy-3-methyl-phenyl | 1 | O | O | CH₂ | 0 | 2 | 0 | phenyl | morpholino | — |
| 2-Hydroxy-phenyl | 1 | O | O | CH₂ | 0 | 2 | 0 | phenyl | morpholino | — |
| 4-Hydroxy-phenyl | 1 | O | O | CH₂ | 0 | 2 | 0 | phenyl | morpholino | — |
| 4-Dimethylamino-phenyl | 1 | O | O | CH₂ | 0 | 2 | 0 | phenyl | morpholino | — |
| 4-Benzylamino-phenyl | 1 | O | O | CH₂ | 0 | 2 | 0 | phenyl | morpholino | — |
| 1H-Tetrazol-5-yl phenyl | 1 | O | O | CH₂ | 0 | 2 | 0 | phenyl | morpholino | — |
| 2-Thienyl | 1 | O | O | CH₂ | 0 | 2 | 0 | phenyl | morpholino | Ex. 55 |
| 3-Furyl | 1 | O | O | CH₂ | 0 | 2 | 0 | phenyl | morpholino | — |
| 4-Pyridyl | 1 | O | O | CH₂ | 0 | 2 | 0 | phenyl | morpholino | — |
| 2-Bromo-phenyl | 1 | O | O | CH₂ | 0 | 2 | 0 | phenyl | diethyl-amino | Ex. 17 |
| 2-Bromo-phenyl | 1 | O | O | CH₂ | 0 | 2 | 0 | phenyl | piperidino | Ex. 21 |
| 2-Bromo-phenyl | 1 | O | O | CH₂ | 0 | 2 | 0 | phenyl | 4-hydroxy-piperidino | Ex. 5 |
| 2-Bromo-phenyl | 1 | O | O | CH₂ | 0 | 2 | 0 | phenyl | 4-methoxy-piperidino | Ex. 42 |
| 2-Bromo-phenyl | 1 | O | O | CH₂ | 0 | 2 | 0 | phenyl | thio-morpholino | Ex. 36 |
| 2-Bromo-phenyl | 1 | O | O | CH₂ | 0 | 2 | 0 | phenyl | homo-morpholino | Ex. 52 |
| 2-Bromo-phenyl | 1 | O | O | CH₂ | 0 | 2 | 0 | 2-fluoro-phenyl | morpholino | — |
| 2-Bromo-phenyl | 1 | O | O | CH₂ | 0 | 2 | 0 | 4-methyl-phenyl | morpho-lino | Ex. 34 |
| 2-Bromo-phenyl | 1 | O | O | CH₂ | 0 | 2 | 0 | 4-chloro-phenyl | morpho-lino | Ex. 19 |
| 2-Bromo-phenyl | 1 | O | O | CH₂ | 0 | 2 | 0 | 2-thienyl | morpholino | — |
| 2-Bromo-phenyl | 1 | O | O | CH₂ | 0 | 2 | 0 | 4-pyridyl | morpholino | — |
| 2-Bromo-phenyl | 1 | N | O | CH₂ | 0 | 2 | 0 | phenyl | morpholino | — |
| 2-Bromo-phenyl | 1 | O | S | CH₂ | 0 | 2 | 0 | phenyl | morpholino | Ex. 44 |
| Phenyl | 2 | O | O | CH₂ | 0 | 2 | 0 | phenyl | morpholino | Ex. 50 |
| 4-Chloro- | 2 | O | O | CH₂ | 0 | 2 | 0 | phenyl | morpholino | — |

-continued

| R¹ | m | X | Y | Z | p | q | n | R² | NR³R⁴ | Example |
|---|---|---|---|---|---|---|---|---|---|---|
| phenyl | | | | | | | | | | |
| 2-Chlorophenyl | 2 | O | O | CH₂ | 0 | 2 | 0 | phenyl | morpholino | Ex. 27 |
| 2-Bromophenyl | 2 | O | O | CH₂ | 0 | 2 | 0 | phenyl | morpholino | Ex. 25 |
| 1-Naphthyl | 2 | O | O | CH₂ | 0 | 2 | 0 | phenyl | morpholino | — |
| 2-Thienyl | 2 | O | O | CH₂ | 0 | 2 | 0 | phenyl | morpholino | — |
| Phenyl | 3 | O | O | CH₂ | 0 | 2 | 0 | phenyl | morpholino | Ex. 57 |
| Phenyl | 4 | O | O | CH₂ | 0 | 2 | 0 | phenyl | morpholino | — |
| Phenyl | 1 | O | O | CH₂ | 1 | 1 | 0 | phenyl | morpholino | Ex. 11 |
| Phenyl | 1 | O | O | CH₂ | 1 | 1 | 0 | 4-chlorophenyl | morpholino | — |
| Phenyl | 1 | O | O | CH₂ | 2 | 0 | 0 | phenyl | morpholino | Ex. 9 |
| Phenyl | 1 | O | O | CH₂ | 0 | 3 | 0 | phenyl | morpholino | — |
| Phenyl | 1 | O | O | CO | 0 | 2 | 0 | phenyl | thiomorpholino | — |
| 2-Bromophenyl | 1 | O | O | CO | 0 | 2 | 0 | phenyl | morpholino | — |
| Phenyl | 1 | O | O | CH₂ | 0 | 2 | 0 | 2-furyl | morpholino | — |
| Phenyl | 1 | O | O | CH₂ | 0 | 2 | 0 | 2-thienyl | morpholino | Ex 61 |
| Phenyl | 1 | O | O | CH₂ | 0 | 2 | 0 | 2-thienyl | thiomorpholino | — |
| Phenyl | 1 | O | O | CH₂ | 0 | 2 | 0 | 2-thienyl | homomorpholino | — |
| Phenyl | 1 | O | O | CH₂ | 0 | 2 | 0 | 2-thienyl | 4-acetylpiperazinyl | — |
| 2-Bromophenyl | 1 | O | O | CH₂ | 0 | 2 | 0 | 3-thienyl | morpholino | — |
| 3-Bromophenyl | 1 | O | O | CH₂ | 0 | 2 | 0 | 2-thienyl | morpholino | — |
| 4-Bromophenyl | 1 | O | O | CH₂ | 0 | 2 | 0 | 2-thienyl | morpholino | — |
| 2-Chlorophenyl | 1 | O | O | CH₂ | 0 | 2 | 0 | 2-thienyl | morpholino | — |
| 3-Chlorophenyl | 1 | O | O | CH₂ | 0 | 2 | 0 | 2-thienyl | morpholino | — |
| 4-Chlorophenyl | 1 | O | O | CH₂ | 0 | 2 | 0 | 2-thienyl | morpholino | — |
| 2-Thienyl | 1 | O | O | CH₂ | 0 | 2 | 0 | phenyl | thiomorpholino | — |
| 3-Bromo-2-thienyl | 1 | O | O | CH₂ | 0 | 2 | 0 | phenyl | morpholino | — |
| 3-Chloro-2-thienyl | 1 | O | O | CH₂ | 0 | 2 | 0 | phenyl | morpholino | — |
| 3-Thienyl | 1 | O | O | CH₂ | 0 | 2 | 0 | phenyl | morpholino | — |
| 2-Thienyl | 1 | O | O | CH₂ | 0 | 2 | 0 | 2-thienyl | morpholino | — |
| 2-Thienyl | 1 | O | O | CH₂ | 0 | 2 | 0 | 2-thienyl | thiomorpholino | — |
| 2-Thienyl | 1 | O | O | CH₂ | 0 | 2 | 0 | 3-thienyl | morpholino | — |
| 2-Thienyl | 2 | O | O | CH₂ | 0 | 2 | 0 | 2-thienyl | morpholino | — |
| 3-Thienyl | 1 | O | O | CH₂ | 0 | 2 | 0 | 2-thienyl | morpholino | — |
| 2-Furyl | 1 | O | O | CH₂ | 0 | 2 | 0 | phenyl | morpholino | — |
| 3-Furyl | 1 | O | O | CH₂ | 0 | 2 | 0 | phenyl | morpholino | — |
| 2-Pyridyl | 1 | O | O | CH₂ | 0 | 2 | 0 | phenyl | morpholino | — |
| 3-Indolyl | 1 | O | O | CH₂ | 0 | 2 | 0 | phenyl | morpholino | — |
| Isopropyl | 0 | O | O | CH₂ | 0 | 2 | 0 | phenyl | morpholino | — |
| Isobutyl | 0 | O | O | CH₂ | 0 | 2 | 0 | phenyl | morpholino | — |
| Isoamyl | 0 | O | O | CH₂ | 0 | 2 | 0 | phenyl | morpholino | — |
| Pentyl | 0 | O | O | CH₂ | 0 | 2 | 0 | phenyl | morpholino | — |
| Phenyl | 1 | O | O | CH₂ | 0 | 2 | 0 | phenyl | 4-acetylpiperazinyl | — |
| Phenyl | 1 | S | O | CH₂ | 0 | 2 | 0 | phenyl | 4-acetylpiperazinyl | — |

Representative examples of the alkylenediamine derivatives having formula (1) wherein "r" is 0, but being not included in the alkylenediamine derivatives of formula (3) are set forth in the following table, wherein "Ex. No" in the column for "Example" refers to the synthesis example number described hereinafter in the specification.

| R¹ | m | X | Y | Z | p | q | n | R² | NR³R⁴ | Example |
|---|---|---|---|---|---|---|---|---|---|---|
| Hydrogen | 0 | O | O | CH₂ | 0 | 2 | 0 | phenyl | morpholino | Ex. 65 |
| Methyl | 0 | O | O | CH₂ | 0 | 2 | 0 | phenyl | morpholino | Ex. 66 |

Representative examples of the alkylenediamine derivatives of the formula (4), which correspond to the alkylenediamine derivatives of the formula (1) wherein "r" is 1, are set forth in the following table, wherein "Ex. No" in the column for "Example" refers to the synthesis example number described hereinafter in the specification.

| $R^1$ | m | X | Y | z | p | q | n | $R^2$ | $NR^3R^4$ | Example |
|---|---|---|---|---|---|---|---|---|---|---|
| Phenyl | 1 | O | O | $CH_2$ | 0 | 2 | 0 | phenyl | morpholino | — |
| 2-Bromo-phenyl | 1 | O | O | $CH_2$ | 0 | 2 | 0 | phenyl | morpholino | No. 70 |
| Phenyl | 1 | O | O | $CH_2$ | 0 | 2 | 0 | 2-thienyl | morpholino | — |
| 2-Thienyl | 1 | O | O | $CH_2$ | 0 | 2 | 0 | phenyl | morpholino | — |
| 2-Thienyl | 2 | O | O | $CH_2$ | 0 | 2 | 0 | phenyl | morpholino | — |
| 2-Thienyl | 2 | O | O | $CH_2$ | 0 | 2 | 0 | 2-thienyl | morpholino | — |

Representative examples of the alkylenediamine derivatives of the formula (5), which correspond to the alkylenediamine derivatives of the formula (2) wherein "r" is 0, are set forth in the following table, wherein "Ex. No" in the column for "Example" refers to the synthesis example number described hereinafter in the specification.

| $R^1$ | m | X | Y | Z | p | q | n | $R^2$ | $NR^3R^4$ | Example |
|---|---|---|---|---|---|---|---|---|---|---|
| Phenyl | 0 | O | O | $CH_2$ | 0 | 2 | 0 | phenyl | morpholino | No. 68 |
| Phenyl | 1 | O | O | $CH_2$ | 0 | 2 | 0 | phenyl | morpholino | No. 69 |
| Phenyl | 1 | S | O | $CH_2$ | 0 | 2 | 0 | phenyl | morpholino | — |
| Phenyl | 1 | O | S | $CH_2$ | 0 | 2 | 0 | phenyl | morpholino | — |
| Phenyl | 1 | S | S | $CH_2$ | 0 | 2 | 0 | phenyl | morpholino | — |
| Phenyl | 1 | O | O | $CH_2$ | 0 | 2 | 0 | phenyl | thiomorpholino | — |
| Phenyl | 1 | O | O | $CH_2$ | 0 | 2 | 0 | phenyl | homomorpholino | — |
| Phenyl | 1 | O | O | $CH_2$ | 0 | 2 | 0 | phenyl | 4-acetyl-piperazinyl | — |
| Phenyl | 1 | O | O | $CH_2$ | 0 | 2 | 0 | furyl | morpholino | — |
| Phenyl | 1 | O | O | $CH_2$ | 0 | 2 | 0 | 2-thienyl | morpholino | — |
| Phenyl | 1 | O | O | $CH_2$ | 0 | 2 | 0 | 2-thienyl | thiomorpholino | — |
| Phenyl | 1 | O | O | $CH_2$ | 0 | 2 | 0 | 3-thienyl | morpholino | — |
| Phenyl | 2 | O | O | $CH_2$ | 0 | 2 | 0 | phenyl | morpholino | — |
| 2-Bromo-phenyl | 1 | O | O | $CH_2$ | 0 | 2 | 0 | phenyl | morpholino | — |
| 2-Bromo-phenyl | 1 | O | O | $CH_2$ | 0 | 2 | 0 | phenyl | thiomorpholino | — |
| 2-Bromo-phenyl | 1 | O | O | $CH_2$ | 0 | 2 | 0 | 2-furyl | morpholino | — |
| 2-Bromo-phenyl | 1 | O | O | $CH_2$ | 0 | 2 | 0 | 2-thienyl | morpholino | — |
| 2-Bromo-phenyl | 2 | O | O | $CH_2$ | 0 | 2 | 0 | 2-thienyl | morpholino | — |
| 2-Bromo-phenyl | 2 | O | O | $CH_2$ | 0 | 2 | 0 | phenyl | morpholino | — |
| 3-Bromo-phenyl | 1 | O | O | $CH_2$ | 0 | 2 | 0 | phenyl | morpholino | — |
| 4-Bromo-phenyl | 1 | O | O | $CH_2$ | 0 | 2 | 0 | phenyl | morpholino | — |
| 2-Chloro-phenyl | 1 | O | O | $CH_2$ | 0 | 2 | 0 | phenyl | morpholino | — |
| 3-Chloro-phenyl | 1 | O | O | $CH_2$ | 0 | 2 | 0 | phenyl | morpholino | — |
| 4-Chloro-phenyl | 1 | O | O | $CH_2$ | 0 | 2 | 0 | phenyl | morpholino | — |
| 4-Fluoro-phenyl | 1 | O | O | $CH_2$ | 0 | 2 | 0 | phenyl | morpholino | — |
| 4-Trifluoromethyl-phenyl | 1 | O | O | $CH_2$ | 0 | 2 | 0 | phenyl | morpholino | — |
| 4-Nitro-phenyl | 1 | O | O | $CH_2$ | 0 | 2 | 0 | phenyl | morpholino | — |
| 1-Naphthyl | 1 | O | O | $CH_2$ | 0 | 2 | 0 | phenyl | morpholino | — |
| 2-Thienyl | 0 | O | O | $CH_2$ | 0 | 2 | 0 | phenyl | morpholino | — |
| 2-Thienyl | 1 | O | O | $CH_2$ | 0 | 2 | 0 | phenyl | morpholino | — |
| 2-Thienyl | 1 | O | O | $CH_2$ | 0 | 2 | 0 | phenyl | thiomor- | — |

-continued

| R¹ | m | X | Y | Z | p | q | n | R² | NR³R⁴ | Example |
|---|---|---|---|---|---|---|---|---|---|---|
| 2-Thienyl | 2 | O | O | CH₂ | 0 | 2 | 0 | phenyl | morpholino | — |
| 5-Bromo-2-thienyl | 1 | O | O | CH₂ | 0 | 2 | 0 | phenyl | morpholino | — |
| 3-Chloro-2-thienyl | 1 | O | O | CH₂ | 0 | 2 | 0 | phenyl | morpholino | — |
| 3-Thienyl | 1 | O | O | CH₂ | 0 | 2 | 0 | phenyl | morpholino | — |
| 2-Furyl | 1 | O | O | CH₂ | 0 | 2 | 0 | phenyl | morpholino | — |
| 3-Furyl | 1 | O | O | CH₂ | 0 | 2 | 0 | phenyl | morpholino | — |
| 2-Thienyl | 1 | O | O | CH₂ | 0 | 2 | 0 | 2-thienyl | morpholino | — |
| 2-Thienyl | 1 | O | O | CH₂ | 0 | 2 | 0 | 2-thienyl | thiomorpholino | — |
| 3-Thienyl | 1 | O | O | CH₂ | 0 | 2 | 0 | 2-thienyl | morpholino | — |
| 2-Furyl | 1 | O | O | CH₂ | 0 | 2 | 0 | 2-thienyl | morpholino | — |
| 2-Thienyl | 1 | O | O | CH₂ | 0 | 2 | 0 | 3-thienyl | morpholino | — |
| 2-Furyl | 1 | O | O | CH₂ | 0 | 2 | 0 | 2-furyl | morpholino | — |
| 2-Pyridyl | 1 | O | O | CH₂ | 0 | 2 | 0 | phenyl | morpholino | — |
| 3-Indolyl | 1 | O | O | CH₂ | 0 | 2 | 0 | phenyl | morpholino | — |
| Isopropyl | 0 | O | O | CH₂ | 0 | 2 | 0 | phenyl | morpholino | — |
| Isobutyl | 0 | O | O | CH₂ | 0 | 2 | 0 | phenyl | morpholino | No 67 |
| Isoamyl | 0 | O | O | CH₂ | 0 | 2 | 0 | phenyl | morpholino | — |
| Pentyl | 0 | O | O | CH₂ | 0 | 2 | 0 | phenyl | morpholino | — |

Representative examples of the alkylenediamine derivatives of the formula (6), which correspond to the alkylenediamine derivatives of the formula (2) wherein "r" is 1, are set forth in the following table, wherein "Ex. No" in the column for "Example" refers to the synthesis example number described hereinafter in the specification.

| R¹ | m | X | Y | Z | p | q | n | R² | NR³R⁴ | Example |
|---|---|---|---|---|---|---|---|---|---|---|
| Phenyl | 1 | O | O | CH₂ | 0 | 2 | 0 | phenyl | morpholino | No. 72 |
| Phenyl | 1 | O | O | CH₂ | 0 | 2 | 0 | 2-thienyl | morpholino | — |
| 2-Bromo-phenyl | 1 | O | O | CH₂ | 0 | 2 | 0 | phenyl | morpholino | — |
| 2-Thienyl | 1 | O | O | CH₂ | 0 | 2 | 0 | phenyl | morpholino | — |
| 2-Thienyl | 1 | O | O | CH₂ | 0 | 2 | 0 | 2-thienyl | morpholino | — |

(I) Test for Inhibition of Urinating Contraction of Bladder

With respect to inhibition of the urinating contraction of bladder, performance of the compound of the present invention was evaluated by the following method.

Method

A male Wistar rat was anesthetized with urethane (1.5 g/kg, s.c.) and fixed on its back on a board. Into the trachea of the rat, a tracheotomy tube was inserted in order to insure an airway, and then midline incisura was carried out to denude the bladder. Subsequently, a small opening was produced on the top of the bladder and the urine was exhausted, and then a polyethylene cannula (diameter: approx. 1 mm) was inserted into the bladder. The urethra and the ureter were tied up to make the bladder a closed system.

By means of an infusion pump, phsiological saline was poured into the bladder of rat at a rate of 0.05 ml/min. induce the rhythmic bladder contraction. Subsequently, intravesical pressure was measured by a pressure transducer and recorded on a pen-writing recorder. The test compound was dissolved in physiological saline and then administered into the femoral vein through a polyethylene cannula.

EVALUATION

Performance for inhibiting the urinary bladder contraction was evaluated by measuring the period (inhibiting period) in which the rhythmic bladder contraction was inhibited. As the medicament, each of the compounds obtained in Examples was used. Each of the measured inhibiting periods is set forth in Table 1.

TABLE 1

| Compound | Dose (mg/kg, i.v.) | Number of Tested rats | Period (min.) | $LD_{50}$/mouse (mg/kg, i.v.) |
|---|---|---|---|---|
| Control (physiological saline) | — | 6 | 1.6 | — |
| Example 2 | 8 | 10 | 5.4 | 76 |
| Example 3 | 8 | 4 | 6.0 | 49 |
| Example 4 | 8 | 4 | 3.8 | 77 |
| Example 13 | 5 | 4 | 6.5 | 48 |
| Example 25 | 8 | 2 | 7.5 | 79 |
| Example 27 | 8 | 2 | 8.0 | 75 |
| Example 46 | 5 | 2 | 6.0 | >20 |
| Example 50 | 5 | 2 | 7.5 | 45 |
| Example 55 | 8 | 4 | 4.6 | 84 |
| Example 56 | 11 | 4 | 4.7 | 111 |
| Example 61 | 6 | 2 | 6.5 | 59 |
| Example 62 | 6 | 2 | 7.2 | 63 |
| Example 67 | 14 | 2 | 3.5 | 137 |
| Example 69 | 8 | 4 | 6.6 | 76 |
| Example 70 | 6 | 2 | 1.5 | >60 |

With respect to toxicity of the compounds of the invention, each $LD_{50}$ (mg/kg) measured by the up-and-down method is also set forth in Table 1.

As is evident from the results in Table 1, the compounds of the invention are effective for inhibiting the urinating contraction.

(II) Effect on Isolated Urinary Bladder Smooth Muscle

Method

Urinary bladder strips were obtained from male Japanese white rabbits (weight: 2.00–2.80 kg). Each strip was suspended in an organ bath containing Krebs solution. The organ bath was maintained at 37° C. and constantly gassed with carbogen. Cumulative concentration-response curves of acetylcholine and norepinephrine were obtained.

The compound to be tested (compound of Example 2 (i.e., 5-benzyl-3-(3-morpholino-1-phenylpropyl)-1,3-oxazolidin-2-one fumarate) was introduced into the Krebs solution five minutes prior to the introduction of acetylcholine or norepinephrine to elicit the contractive action.

Evaluation

The pretreatment of the tested compound at a concentration in the range of $1 \times 10^{-5}$ to $3 \times 10^{-5}$ did not give any effective action on the contraction caused by acetylcholine and norepineperine. Therefore, it has been confirmed that the tested compound depresses the bladder contraction not by acting on the peripheral nerves system but on the central nutyes system.

Thus, the alkylenediamine derivative of the formula (1) and its pharmaceutically acceptable salt can be favorably employed as a remedy for dysuria.

The remedy for dysuria of the invention can be used either in a general preparation form for oral administration or in the form for parenteral administration such as injections and suppositories. Preparation forms for oral administration may be tablets, capsules, powder, granules, syrup and the like. Preparation forms for parenteral administration may be injections and suppositories and the like. For the formulation of these preparations, excipients, disintegrants, binders, lubricants, pigments, diluents and the like which are commonly employed in the art may be used. The excipients may include dextrose, lactose and the like. Starch, carboxymethylcellulose calcium and the like may be used as the disintegrants. Magnesium stearate, talc and the like may be used as the lubricants. The binders may be hydroxypropylcellulose, gelatin, polyvinylpyrrolidone and the like.

The dose may usually be about 0.1 mg/day to 10.0 mg/day in the case of an injectable preparation and about 1.0 mg/day to 500 mg/day in the case of oral administration, both for an adult. The dose may be either increased or decreased depending upon the age and conditions of patients.

The remedy for dysuria of the invention is a centrally acting medicament which does not lower the blood pressure and which selectively acts on the bladder.

The following examples further illustrate the present invention in more detail.

EXAMPLE 1

5-Benzyl-3-(3-morpholino-1-phenylpropyl)-1,3-oxazolidin-2-one

5-Benzyl-1,3-oxazolidin-2-one (825 mg, 4.7 mmol), 4-[(3-chloro-3-phenyl) propyl] morpholine hydrochloride (1,415 mg, 5.1 mmol), potassium carbonate (2.12 g, 15.4 mmol) and methyl ethyl ketone (25 ml) were mixed and then heated to react under reflux for 23 hours. After the resulting solution was cooled to room temperature, insolubles were removed by filtration and the solvent was removed by distillation under reduced pressure. To the obtained residue, ethyl acetate was added. The resulting mixture was washed sequentially with water and saturated aqueous sodium chloride, and then dried over anhydrous sodium sulfate. The solvent was removed by distillation under reduced pressure, and the residue was purified by silica gel column chromatography (ethyl acetate) to give 376 mg of diastereomer A as a colorless oil (yield: 21%) and 556 mg of diastereomer B as a pale yellow oil (yield: 31%).

$^1$H-NMR (CDCl$_3$) δ: diastereomer A 1.8–2.5 (8H, m), 2.8–3.2 (4H, m), 3.5–3.8 (4H, m), 4.64 (1H, m) 5.00 (1H, t, J=7 Hz), 7.0–7.4 (10H, m).

diastereomer B 1.7–3.1 (11H, m), 3.42 (1H, t, J=8 Hz), 3.5–3.8 (4H, m), 4.68 (1H, m) 5.00 (1H, t, J=7 Hz), 6.8–7.4 (10H, m).

EXAMPLE 2

5-Benzyl-3-(3-morpholino-1-phenylpropyl)-1,3-oxazolidin-2-one fumarate

5-Benzyl-3-(3-morpholino-1-phenylpropyl)-1,3-oxazolidin-2-one (diastereomer A) (376 mg, 1.0 mmol) prepared in Example 1 was dissolved in ethanol (5 ml). To the solution, fumaric acid (115 mg, 1.0 mmol) was added and dissolved under heating. From the resulting solution, ethanol was removed by distillation under reduced pressure, and then the residue was crystallized from ethanol/hexane (3/1). The obtained crystalline product was collected by filtration, washed with ethanol/hexane (3/1), and dried under reduced pressure overnight at room temperature to give 234 mg of the titled compound as a white crystalline powder (yield: 46%).

m.p.: 133°–135° C. (decomp.)

$^1$H-NMR (CDCl$_3$) δ:

1.9–2.3 (2H, m), 2.4–2.7 (2H, m), 2.7–3.1 (6H, m), 3.1–3.4 (2H, m), 3.6–3.9 (4H, m), 4.5–5.0 (2H, m), 6.84 (2H, s), 7.1–7.4 (10H, m).

IR (KBr) cm$^{-1}$:

3420, 2920, 2580, 1725, 1425, 1360, 1290, 1250, 1215, 1040, 980, 970, 750, 700, 640.

EXAMPLE 3

(−)-5-Benzyl-3-(3-morpholino-1-phenylpropyl)-1,3-oxazolidin-2-one fumarate

5-Benzyl-3-(3-morpholino-1-phenyl-propyl)-1,3-oxazolidin-2-one (diastereomer A) (2.89 g) prepared in the same manner as is described in Example 1 was dissolved in a mixed solvent (isopropyl alcohol/acetone/water=50 g/20 g/6.2 g)(15 ml). To the prepared solution, D(−)-tartaric acid (1.17 g) dissolved in the above mixed solvent (30 ml) was added. After the resulting solution was allowed to stand for 3 hours at room temperature, the deposited crystals were collected by filtration, washed with the above mixed solvent (45 ml), and air-dried to give a white crystalline powder (1.82 g).

The white crystalline powder (2.39 g) prepared in the same manner as above was added to the above mixed solvent (65 ml) and dissolved at 80° C. After the resulting solution was allowed to stand overnight at room temperature, the deposited crystals were collected by filtration, washed with the above mixed solvent (15 ml) and dried under reduced pressure to obtain a white powder (2.1 g). The obtained white powder was suspended in water (50 ml). The suspension was made alkaline by addition of saturated aqueous sodium bicarbonate, and then extracted twice with dichloromethane (30 ml). The extract was washed with saturated aqueous sodium chloride, and then dried over anhydrous sodium sulfate. Subsequently, the solvent was removed by distillation under reduced pressure to obtain an oily product (1.5 g). The obtained oily product was dissolved in ethanol (10 ml). To the resulting solution, fumaric acid (458 mg) in ethanol (10 ml) was added. After n-hexane (5 ml) was further added, the solution was stirred overnight at room temperature. The deposited crystals were collected by filtration, washed with ethanol/n-hexane (4/1) (15 ml) and ethanol/n-hexane (1/1) (10 ml), air-dried and dried under reduced pressure overnight at 50° C. to give the titled compound (1.1 g).

m.p.: 131°–132 ° C. (decomp.)

$[\alpha]_D^{23}$: −1° (C. 0.6, methanol)

HPLC: A free body was detected.

| column: | CHIRALCEL OG | monitoring: | at 254 nm |
|---|---|---|---|
| eluent: | n-hexane/ethanol = 5/1 | | |
| rate: | 1 ml/minute | temperature: | r.t. |
| $t_R$: | 19.5 minutes | | |

$^1$H-NMR (CD$_3$OD) δ:

2.1–2.2 (2H, m), 2.4–2.6 (2H, m), 2.8–3.3 (8H, m), 3.7–3.9 (4H, m), 4.7–4.9 (2H, m), 6.73 (2H, s), 7.2–7.4 (10H, m).

IR (KBr) cm$^{-1}$:

3400, 1730, 1710, 1425, 1245, 980, 750, 690, 640.

EXAMPLE 4

(+)-5-Benzyl-3-(3-morpholino-1-phenylpropyl)-1,3-oxazolidin-2-one fumarate

The filtrate obtained by the step of collecting the crystals prepared by the reaction of diastereomer A and D(−)-tartaric acid in Example 3 was evaporated under reduced pressure at the temperature of not more than 45° C. so as to remove the solvent, and then water was added to the resulting oily product. The obtained mixture was made alkaline by addition of saturated aqueous sodium bicarbonate, and then extracted twice with dichloromethane (30 ml). The extract was washed with saturated aqueous sodium chloride, and then dried over anhydrous sodium sulfate. Subsequently, the solvent was removed by distillation under reduced pressure to obtain an oily product (1.64 g). The oily product dissolved in a mixed solvent (isopropyl alcohol/acetone/water =50 g/20 g/6.2 g) (15 ml). To the prepared solution, L(+)-tartaric acid (647 mg) in the above mixed solvent (16 ml) was added. After the resulting solution was allowed to stand overnight at room temperature, the deposited crystals were collected by filtration, washed with the above mixed solvent (25 ml), and air-dried to obtain a white crystalline powder (1.78 g).

The white crystalline powder (2.28 g) prepared in the same manner as above was added to the above mixed solvent (62 ml) and dissolved at 80° C. After the resulting solution was allowed to stand overnight at room temperature, the deposited crystals were collected by filtration, washed with the above mixed solvent (15 ml) and dried under reduced pressure to obtain a white powder (2.08 g). The obtained white powder was suspended in water (50 ml). The suspension was made alkaline by addition of saturated aqueous sodium bicarbonate, and then extracted twice with dichloromethane (30 ml). The extract was washed with saturated aqueous sodium chloride, and then dried over anhydrous sodium sulfate. Subsequently, the solvent was removed by distillation under reduced pressure to obtain an oily product (1.49 g). The obtained oily product was dissolved in ethanol (10 ml). To the resulting solution, fumaric acid (455 mg) in ethanol (10 ml) was added. After n-hexane (5 ml) was further added, the solution was stirred overnight at room temperature. The deposited crystals were collected by filtration, washed with ethanol/n-hexane (4/1) (15 ml) and ethanol/n-hexane (1/1) (10 ml), air-dried and dried under reduced pressure overnight at 50° C. to obtain the titled compound (1.08 g).

m.p.: 133°–135° C. (decomp.)

$[\alpha]_D^{23}$: +1° (c. 0.6, methanol)

HPLC: A free body was detected.

| column: | CHIRALCEL OG | monitoring: | at 254 nm |
|---|---|---|---|
| eluent: | n-hexane/ethanol = 5/1 | | |
| rate: | 1 ml/minute | temperature: | r.t. |
| $t_R$: | 21.3 minutes | | |

$^1$H-NMR (CD$_3$OD) δ:

2.1–2.2 (2H, m), 2.4–2.6 (2H, m), 2.8–3.3 (8H, m), 3.7–3.9 (4H, m), 4.7–4.9 (2H, m), 6.73 (2H, s), 7.2–7.4 (10H, m).

IR (KBr) cm$^{-1}$:

3400, 1730, 1710, 1440, 1420, 1240, 970, 745, 690, 625.

EXAMPLE 5

5-(2-Bromophenyl)methyl-3-[3-(4-hydroxypiperidino)-1-phenylpropyl]-1,3-oxazolidin-2-one (1) 5-(2-Bromophenyl)methyl-3-(3-chloro-1-phenylpropyl)-1,3-oxazolidin-2-one 5-(2-Bromophenyl)methyl-1,3-oxazolidin-2-one (256 mg, mmol), 1-bromo-3-chloro-1-phenylpropene (234 mg, 1 mmol), cesium carbonate (326 mg, 1 mmol) and 2 ml of dimethylformamide dried over alumina were mixed and then stirred to cause reaction at room temperature for 4 days. After water was added, the resulting mixture was extracted with ethyl acetate. The organic portion was sequentially washed with water and saturated aqueous sodium chloride, and then dried over anhydrous sodium sulfate. The solvent was then removed by distillation under reduced pressure to obtain 470 mg of a colorless oily product. The product was purified by medium pressure silica gel column chromatography with a mixed solvent of ethyl acetate/hexane (1/2) to obtain 121 mg of a colorless oil (yield: 29.7).

$^1$H-NMR (CDCl$_3$) δ:

2.3–2.6 (2H, m), 2.9–3.4 (4H, m), 3.4–3.6 (2H, m), 4.7–4.8 (1H, m), 5.0–5.1 (1H, m), 7.0–7.4 (8H, m), 7.5–7.6 (1H, m).

IR (KBr) cm$^{-1}$:

2950, 1740, 1485, 1470, 1420, 1360, 1240, 1030, 750, 695.

(2) 5-(2-Bromophenyl)methyl-3-[3-(4-hydroxypiperidino)-1-phenylpropyl]-1,3-oxazolidin-2-one 5-(2-Bromophenyl)methyl-3-(3-chloro-1-phenylpropyl)-1,3-oxazolidin-2-one (0.81 g, 1.7 mmol) prepared in the above (1) and 4-hydroxypiperidine (0.52 g, 5.1 mmol) were dissolved in dichloromethane, and then dichloromethane was removed by distillation under reduced pressure. After the obtained mixture was stirred at 110° C. for 5 hours, ethyl acetate was added and extracted with 1N hydrochloric acid. The aqueous portion was made alkaline by addition of saturated aqueous sodium bicarbonate, and then extracted with dichloromethane. The organic portion was sequentially washed with water and saturated aqueous sodium chloride, and then dried over anhydrous sodium sulfate. The solvent was then removed by distillation under reduced pressure to obtain a white amorphous product (0.83 g). The product was purified by medium pressure silica gel column chromatography with a mixed solvent of methanol/chloroform (1/40) to obtain 0.41 g of a colorless oil (yield: 51%), which was referred to as diastereoisomer A. Further, 0.36 g of a pale yellow oil of diastereomer B was also obtained by medium pressure silica gel column chromatography using a mixed solvent of methanol/chloroform (1/20) (yield: 45%).

Diastereomer A
$^1$H-NMR (CDCl$_3$) δ:
1.5–1.7 (2H, m), 1.8–2.0 (2H, m), 2.0–2.2 (4H, m), 2.2–2.4 (2H, m), 2.6 (1H, broad s), 2.7–2.9 (2H, m), 3.1–3.3 (4H, m), 3.6–3.8 (1H, m), 4.6–4.8 (1H, m), 5.00 (1H, dd, J=7 Hz, 9 Hz), 7.1–7.2 (1H, m), 7.2–7.4 (7H, m), 7.54 (1H, d, J=8 Hz).
IR (neat) cm$^{-1}$:
3400, 2930, 2810, 1730, 1470, 1420, 1360, 1240, 1070, 1035, 750, 695, 660.

Diastereomer B
$^1$H-NMR (CDCl$_3$) δ:
1.5–1.7 (2H, m), 1.8–2.0 (2H, m), 2.0–2.3 (4H, m), 2.3–2.5 (2H, m), 2.7–3.0 (5H, m), 3.04 (1H, dd, J=6 Hz, 14 Hz), 3.53 (1H, dd, J=8 Hz, 9 Hz), 3.6–3.8 (1H, m), 4.7–4.9 (1H, m), 4.99 (1H, dd, J=7 Hz, 8 Hz), 7.0–7.2 (3H, m), 7.2–7.4 (5H, m), 7.45 (1H, dd, J=1 Hz, 8 Hz).
IR (neat) cm$^{-1}$:
3400, 2930, 2810, 1730, 1470, 1420, 1360, 1240, 1070, 1035, 750, 695, 660.

EXAMPLE 6

5-(2-Bromophenyl)methyl-3-[3-(4-hydroxypiperidino)-1-phenylpropyl]-1,3-oxazolidin-2-one fumarate 5-(2-Bromophenyl)methyl-3-[3-(4-hydroxypiperidino)-1-phenylpropyl]-1,3-oxazolidin-2-one (237 mg, 0.5 mmol) prepared in the same manner as is described in Example 5 and fumaric acid (53 mg, 0.5 mmol) were dissolved in ethanol (3 ml) under heating. From the resulting solution, ethanol was removed by distillation under reduced pressure. Water was added to the residue and then the resulting solution was concentrated. After the concentration was repeated for three times, the residue was dried in vacuum. The dried residue was crushed to obtain 280 mg of the titled compound as a white powder.

$^1$H-NMR (D$_2$O) δ:
1.6–2.4 (6H, m), 2.7–3.6 (10H, m), 3.8–4.0 (1H, m), 4.1–4.3 (1H, m), 6.67 (2H, s), 7.2–7.5 (8H, m), 3.1–3.3 (4H, m), 3.6–3.8 (1H, m), 7.6–7.7 (1H, m).
IR (neat) cm$^{-1}$:
3400, 2940, 1735, 1570, 1425, 1365, 1250, 1040, 980, 755, 700, 645.

EXAMPLE 7

3-(3-Morpholino-1-phenylpropyl)-5-phenyl-1,3-oxazolidin-2-one (1) 2-(3-Morpholino-1-phenylpropyl)amino-1-phenylethanol 2-Amino-1-phenylethanol (2.50 g, 18.2 mmol) and 4-(3-chloro-3-phenylpropyl)morpholine (4.37 g, 18.2 mmol) were mixed and heated to cause reaction at 110° C. for 40 minutes. The resulting mixture was cooled to room temperature, and then dissolved into chloroform (200 ml). After the solution was chilled with ice, 1N NaOH was added so that the hydrochloride was libereated. The chloroform portion was collected and dried over anhydrous sodium sulfate. The solvent was then removed by distillation under reduced pressure. The residue was purified by medium pressure silica gel column chromatography (chloroform/methanol=100/1) to obtain 2.88 g of the titled compound as a yellow oil (Yield: 46.5%).

$^1$H-NMR (CDCl$_3$) δ:
1.75–2.79 (10H, m), 3.67–3.72 (4H, m), 3.80–3.84 (1H, m), 4.64–4.78 (1H, m), 7.24–7.34 (10H, m).

(2) 3-(3-Morpholino-1-phenylpropyl)-5-phenyl-1,3-oxazolidin-2-one 2-(3-Morpholino-1-phenylpropyl)amino-1-phenylethanol (2.2 g, 6.46 mmol) prepared in the above (1), ether (100 ml) and 10% NaOH (50 ml) were mixed and stirred. To the obtained mixture, 20% toluene solution of trichloromethyl chloroformate [14 ml (14 mmol)] was dropwise added slowly for a period of 1 hour. After stirring at room temperature for 1 hour, ethyl acetate (200 ml) was added to the resulting solution, and then the ethyl acetate portion was collected. The obtained portion was washed with saturated aqueous sodium chloride (100 ml) and then dried over anhydrous sodium sulfate. After the solvent was removed by distillation under reduced pressure, the residue was purified by medium pressure silica gel column chromatography (chloroform/methanol=50/1) to obtain 510 mg of diastereoruer A (yield: 21.5%) and 390 mg of diastereomer B (yield: 16.5%) of the titled compound as oily products, provided that the diastereoisomers showing the Rf values of about 0.6 and 0.5 in TLC (chloroform/methanol=10/1) were referred to as diastereoisomers A and B, respectively.

Diastereomer A
$^1$H-NMR (CDCl$_3$) δ:
2.06–2.39 (8H, m), 3.36–3.58 (2H, m), 3.67–3.69 (4H, m), 5.12 (1H, t, J=7 Hz), 5.36–5.40 (1H, m), 7.26–7.41 (10H, m).

Diastereomer B
$^1$H-NMR (CDCl$_3$) δ:
2.23–2.70 (8H, m), 3.73–3.82 (4H, m), 2.98–3.02 and 3.84–3.87 (2H, m), 5.07–5.11 (1H, m), 5.46–5.51 (1H, m). 7.16–7.34 (10H, m).

EXAMPLE 8

3-(3-Morpholino-1-phenylpropyl)-5-phenyl-1,3-oxazolidin-2-one fumarate

Diastereomer A of 3-(3-morpholino-1-phenylpropyl)-5-phenyl-1,3-oxazolidin-2-one (480 mg, 1.31 mmol) prepared in the same manner as is described in Example 7 and fumaric acid (152 mg, 1.31 mmol) were dissolved in ethanol (30 ml). The resulting solution was concentrated by distillation under reduced pressure to obtain 389 mg of the titled compound as a pale yellow amorphous product (yield: 61.5%).

$^1$H-NMR (CDCl$_3$) δ:
2.31–2.78 (8H, m), 3.47–3.77 (6H, m), 5.00–5.04 (1H, m), 5.50–5.54 (1H, m), 6.71 (2H, s), 7.36–7.42 (10H, m),
IR (KBr) cm$^{-1}$:
3420, 1740, 1250, 990, 700.

EXAMPLE 9

5-Benzyl-3-(3-morpholino-3-phenylpropyl)-1,3-oxazolidin-2-one (1) 5-Benzyl-3-(3-oxo-3-phenylpropyl)-1,3-oxazolidin-2-one 5-Benzyl-1,3-oxazolidin-2-one (1.77 g, 10 mmol), 3-chloropropiophenone (1.69 g, 10 mmol), potassium carbonate powder (2.76 g, 20 mmol) and methyl ethyl ketone (50 ml) were mixed and then heated to cause reaction under reflux for 16 hours. The solvent was removed by distillation under reduced pressure and the obtained residue was dissolved in ethyl acetate and water. The organic portion was washed sequentially with water and saturated aqueous sodium chloride, and then dried over anhydrous sodium sulfate. The solvent was removed by distillation under reduced pressure to obtain 3.00 g of a pale yellow oily product. The obtained product was purified by silica gel column chromatography using hexane/ethyl acetate=1/1 to obtain 2.05 g of the titled compound as a colorless oil (yield: 66.3%).

$^1$H-NMR (CDCl$_3$) δ:

2.9–3.3 (4H, m), 3.3–3.5 (1H, m), 3.5–3.7 (3H, m), 4.6–4.8 (1H, m), 7.1–7.4 (5H, m), 7.4–7.7 (3H, m), 7.92 (7H, d, J=7 Hz).

IR (KBr) cm$^{-1}$:

1740, 1680, 1590, 1480, 1440, 1360, 1250, 1200, 1020, 740, 695.

(2) 5-Benzyl-3-(3-hydroxy-3-phenylpropyl)-1,3-oxazolidin-2-one

5-Benzyl-3-(3-oxo-3-phenylpropyl)-1,3-oxazolidin-2-one (0.31 g, 1 mmol) prepared in the above (1) was dissolved in 3 ml of ethanol. To the solution, sodium boron hydride (80 mg, 2 mmol) was added under stirring while chilling with ice. After the resulting solution was stirred to cause reaction at room temperature for 30 minutes, water was added. The obtained solution was extracted with ethyl acetate. The organic portion was sequentially washed with water and saturated aqueous sodium chloride, and then dried over anhydrous sodium sulfate. The solvent was then removed by distillation under reduced pressure to obtain 0.31 g of the titled compound as a colorless oil (yield: 100%).

$^1$H-NMR (CDCl$_3$) δ:

1.7–1.9 (2H, m), 2.8–3.1 (3H, m), 3.2–3.3 (2H, m), 3.4–3.6 (2H, m), 4.5–4.6 (1H, m), 4.6–4.8 (1H, m), 7.2–7.4 (10H, m).

IR (KBr) cm$^{-1}$:

3400, 3020, 2920, 1730, 1480, 1445, 1370, 1250, 1210, 1060, 1020, 750, 690.

(3) 5-Benzyl-3-(3-chloro-3-phenylpropyl)-1,3-oxazolidin-2-one

5-Benzyl-3-(3-hydroxy-3-phenylpropyl)-1,3-oxazolidine-2-one (0.31 g, 1 mmol) prepared in the above (2) was dissolved in dichloromethane (3 ml). To the solution, thionyl chloride (0.08 ml, 1.1 mmol) was added and stirred at room temperature for 30 minutes. After water was added, the obtained solution was extracted with ethyl acetate. The organic portion was sequentially washed with saturated aqueous sodium bicarbonate and saturated aqueous sodium chloride, and then dried over sodium sulfate. The solvent was then removed by distillation under reduced pressure to obtain 0.34 g of the titled compound as a colorless oil (yield: 100%).

$^1$H-NMR (CDCl$_3$) δ:

2.1–2.3 (2H, m), 2.8–3.2 (2H, m), 3.2–3.6 (4H, m), 4.6–4.9 (2H, m), 7.1–7.4 (10H, m).

IR (KBr) cm$^{-1}$:

3020, 2910, 1740, 1485, 1450, 1430, 1370, 1260, 1025, 750, 695.

(4) 5-Benzyl-3-(3-morpholino-3-phenylpropyl)-1,3-oxazolidin-2-one

5-Benzyl-3-(3-chloro-3-phenylpropyl)-1,3-oxazolidin-2-one (0.34 g, 1 mmol) prepared in the above (3) and morpholine (0.26 g, 3 mmol) were mixed and heated to cause reaction at 110° C. for 3 hours. The resulting solution was dissolved in ethyl acetate and 1N hydrochloric acid. The aqueous portion was made alkaline by addition of potassium carbonate, and then extracted twice with ethyl acetate. The obtained organic portions of the extractions were combined and washed sequentially with water and saturated aqueous sodium chloride, and then dried over sodium sulfate. The solvent was removed by distillation under reduced pressure to obtain 0.31 g of a red oily product. The product was purified by silica gel column chromatography using ethyl acetate to obtain 0.29 g of the titled compound as a colorless oil (yield: 76%).

$^1$H-NMR (CDCl$_3$) δ:

1.8–2.1 (2H, m), 2.3–2.5 (4H, m), 2.8–3.3 (4H, m), 3.3–3.4 (1H, m), 3.6–3.8 (4H, m), 4.5–4.7 (1H, m), 7.1–7.4 (10H, m)

IR (KBr) cm$^{-1}$:

2950, 2850, 2800, 1740, 1490, 1450, 1430, 1250, 1110, 1030, 750, 700.

EXAMPLE 10

5-Benzyl-3-(3-morpholino-3-phenylpropyl)-1,3-oxazolidin-2-one fumarate 5-benzyl-3-(3-morpholino-3-phenylpropyl)-1,3-oxazolidin-2-one (0.26 g, 0.68 mmol) prepared in the same manner as is described in Example 9 and fumaric acid (0.08 g, 0.68 mmol) were dissolved in ethanol. From the resulting solution, ethanol was removed by distillation under reduced pressure. Water was added to the residue and then the resulting solution was concentrated. After the concentration was repeated for three times, the residue was dried in vacuum to obtain 0.34 g of the titled compound as a pale scarlet amorphous product (yield: 100%).

$^1$H-NMR (CDCl$_3$) δ:

2.6–3.3 (8H, m), 3.4–4.2 (7H, m), 4.6–4.8 (1H, m), 6.69 (2H, s), 7.2–7.6 (10H, m),

IR (KBr) cm$^{-1}$:

3420, 1735, 1450, 1270, 1255, 700.

EXAMPLE 11

5-Benzyl-3-(3-morpholino-2-phenylpropyl)-1,3-oxazolidin-2-one fumarate (1) Ethyl 3-chloro-2-phenylpropionate To ethyl 3-hydroxy-2-phenylpropionate (2.55 g, 13.1 mmol) in dichloromethane (15 ml), SOCl$_2$ (1.87 g, 15.7 mmol) in dichloromethane (1 ml) was added while chilling with ice. After the resulting solution was stirred to cause reaction at room temperature for 3 hours, saturated aqueous sodium bicarbonate was added while chilling with ice. The prepared solution was extracted with dichloromethane, and the extract was washed with saturated aqueous sodium chloride, and then dried over anhydrous sodium sulfate. Subsequently, the solvent was removed by distillation under reduced pressure to obtain a crude product. The product was purified by silica gel column chromatography using acetone/hexane=1/3 to obtain 1.27 g of the titled compound as a colorless oil (yield: 45.5%).

MS (m/e) 176 (M$^+$–Cl)

$^1$H-NMR (CDCl$_3$) δ:

1.2–1.3 (3H, m), 3.9–4.0 (1H, m), 4.1–4.3 (3H, m), 4.4–4.6 (1H, m), 7.3–7.5 (5H, m)

(2) Ethyl 3-morpholino-2-phenylpropionate

A mixture of ethyl 3-chloro-2-phenylpropionate (1 g, 4.72 mmol) prepared in the above (1) and morpholine (470 mg, 5.4 mmol) was stirred to cause reaction for 6 hours under heating at 110° C. To the resulting solution, saturated aqueous sodium bicarbonate was added. After the prepared solution was extracted with ethyl ether, the extract was washed with saturated aqueous sodium chloride, and then dried over anhydrous sodium sulfate. Subsequently, the solvent was removed by distillation under reduced pressure to obtain a crude product. The product was purified by silica gel column chromatography using acetone/hexane=1/6 to obtain 660 mg of the titled compound as a colorless oil (yield: 53.2%).

$^1$H-NMR (CDCl$_3$) δ:

1.2–1.3 (3H, m), 2.4–2.5 (2H, m), 2.5–2.7 (3H, m), 3.16 (1H, dd, J=10 Hz, 5 Hz), 3.6–3.7 (4H, m), 3.82 (1H, dd, J=5 Hz, 5 Hz), 4.1–4.8 (2H, m), 7.2–7.4 (5H, m).

(3) 1-Hydroxy-3-morpholino-2-phenylpropane

Ethyl 3-morpholino-2-phenylpropionate (660 mg, 2.51 mmol) prepared in the above (1) in dry ether (5 ml) was dropwise added to a suspension of LiAlH$_4$ (110 mg, 2.89 mmol) and dry ether (10 ml) while chilling with ice, and then stirred to cause reaction at room temperature for 2 hours. To the resulting solution, saturated aqueous sodium sulfate was added in order to decompose remaining excess LiAlH$_4$. Subsequently, insolubles were removed by filtration. The solvent was removed by distillation under reduced pressure to obtain 660 mg of the titled compound as a colorless oil (yield: 100%).

$^1$H-NMR (CDCl$_3$) δ:

2.4–2.5 (2H, m), 2.6–2.9 (3H, m), 2.69 (1H, t, J=12 Hz), 3.2–3.3 (1H, m), 3.7–3.8 (4H, m), 3.8–3.9 (1H, m), 4.0–4.1 (1H, m), 7.2–7.4 (5H, m).

(4) 1-Chloro-3-morpholino-2-phenylpropane

To a solution of 1-hydroxy-3-morpholino-2-phenylpropane (650 mg, 2.94 mmol) prepared in the above (3) dissolved in dichloromethane (10 ml), SOCl$_2$ (420 mg, 3.53 mmol) in dichloromethane (5 ml) was added while chilling with ice. After the resulting solution was stirred to cause reaction at room temperature for 23 hours, saturated aqueous sodium bicarbonate was added while chilling with ice. The prepared solution was extracted with dichloromethane, and the extract was washed with saturated aqueous sodium chloride, and then dried over anhydrous sodium sulfate. Subsequently, the solvent was removed by distillation under reduced pressure to obtain a crude product. The product was purified by silica gel column chromatography using acetone/hexane=1/5 to obtain 540 mg of the titled compound as a colorless oil (yield: 76.6%).

$^1$H-NMR (CDCl$_3$) δ:

2.3–2.5 (2H, m), 2.5–2.6 (3H, m), 2.96 (1H, m), 3.1–3.2 (1H, m), 3.6–3.8 (4H, m), 3.8–3.9 (1H, m), 3.9–4.0 (1H, m), 7.2–7.4 (5H, m).

(5) 5-Benzyl-3-(3-morpholino-2-phenylpropyl)-1,3-oxazolidin-2-one fumarate

A mixture of 1-chloro-3-morpholino-2-phenylpropene (478 mg) prepared in the above (4), 5-benzyl-1,3-oxazolidine-2-one (354 mg), potassium carbonate (276 mg) and methyl ethyl ketone (10 ml) was heated to cause reaction under reflux for 15.5 hours. To the resulting solution, ethyl acetate was added. The resulting mixture was washed sequentially with water and saturated aqueous sodium chloride, and then dried over anhydrous sodium sulfate. The solvent was removed by distillation under reduced pressure, and the residue was purified by silica gel column chromatography using n-hexane/acetone=3/1 to obtain 268 mg of an oily product (yield: 35.4%). The product was dissolved in ethanol (2 ml), and then fumaric acid (82 mg) in ethanol (3 ml) was added and stirred at room temperature. The deposited crystals were collected by filtration and dried overnight under reduced pressure at 50° C. to obtain 250 mg of the titled compound as a white crystalline powder (yield: 25.2%).

m.p.: 151°–153° C.

$^1$H-NMR (CD$_3$OD) δ:

2.5–2.9 (8H, m), 3.1–3.3 (6H, m), 3.5–3.8 (5H, m), 4.5–4.7 (1H, m), 6.70 (2H, s), 7.0–7.4 (10H, m).

IR (KBr) cm$^{-1}$:

3420, 1735, 1440, 1260, 1110, 1070, 980, 755, 695, 620.

In each of the following Examples 12–54, described are only the name of the prepared compound, its character and the yield of the preparation. The compounds of Examples 40, 44 and 45, the compounds of Examples 41, 42, 43, 52 and 53 and the compounds of the other Examples were prepared in the same manners as described in Examples 7 and 8, in Examples 5 and 6 and in Examples 1 and 2, respectively.

EXAMPLE 12

5-Benzyl-3-(3-morpholino-1-phenylpropyl)-1,3-oxazolidin-2,4-dione fumarate

Yield: 68.7% (pale yellow powder)

m.p.: 158°–160° C.

IR (KBr) cm$^{-1}$:

1800, 1725, 1445, 1395, 1370, 1340, 1255, 1165, 1120, 1065, 975, 745, 690.

$^1$H-NMR (CD$_3$OD) δ:

2.2–2.6 (4H, m), 2.6–2.8 (4H, m), 3.1–3.4 (2H, m), 3.6–3.8 (4H, m), 4.9–5.1 (1H, m), 5.2–5.3 (1H, m), 6.73 (2H, s), 7.0–7.3 (10H, m).

EXAMPLE 13

5-(2-Bromophenyl)methyl-3-(3-morpholino-1-phenylpropyl)-1,3-oxazolidin-2-one fumarate (diastereomer A)

Yield: 14.6% (white powder)

m.p.: 173°–174° C. (decomp.)

IR (KBr, free body) cm$^{-1}$:

3500, 2950, 1740, 1440, 1360, 1240, 1110, 1010, 920, 870, 750,700.

$^1$H-NMR (CD$_3$OD) δ:

2.2–2.5 (2H, m), 2.7–2.9 (2H, m), 2.9–3.4 (8H, m), 3.7–3.9 (4H, m), 5.8–5.9 (1H, m), 6.70 (2H, s), 7.0–8.6 (9H, m).

EXAMPLE 14

5-(2-Bromophenyl)methyl-3-(3-morpholino-1-phenylpropyl)-1,3-oxazolidin-2-one fumarate (diastereomer B)

Yield: 11.2% (amorphous)

IR (KBr, free body) cm$^{-1}$:

2950, 2855, 2810, 1740, 1425, 1370, 1245, 1120, 1040, 750, 700.

$^1$H-NMR (CD$_3$OD) δ:

2.2–2.5 (2H, m), 2.7–3.4 (9H, m), 3.65 (1H, t, J=7 Hz), 3.75–3.85 (4H, m), 4.7–5.0 (2H, m), 6.75 (2H, s), 7.2–7.5 (9H, m).

EXAMPLE 15

5-(2-Chlorophenyl)methyl-3-(3-morpholino-1-phenyl-propyl)-1,3-oxazolidin-2-one fumarate (diastereomer A)

Yield: 67% (white powder)

m.p.: 164°–166° C.

IR (KBr) cm$^{-1}$:

3420, 1735, 1720, 1425, 1250, 1050, 980, 755.

$^1$H-NMR (CD$_3$OD) δ:

2.1–2.6 (2H, m), 2.6–3.5 (10H, m), 3.6–4.1 (4H, m), 4.5–5.0 (2H, m), 6.68 (2H, s), 6.9–7.6 (9H, m).

EXAMPLE 16

5-(2-Chlorophenyl)methyl-3-(3-morpholino-1-phenyl-propyl)-1,3-oxazolidin-2-one fumarate (diastereomer B)

Yield: 47.8% (white powder)

m.p.: 162°–164° C.

IR (KBr) cm$^{-1}$:

3430, 1735, 1710, 1425, 1225, 1075, 760.

$^1$H -NMR (D$_2$O) δ:

2.1–2.6 (2H, m), 2.7–3.5 (9H, m), 3.72 (1H, t, J=8 Hz), 3.6–4.1 (4H, m), 4.8–5.1 (1H, m), 6.58 (2H, s) 7.0–7.51 (9H, m).

EXAMPLE 17

5-(2-Bromophenyl)methyl-3-(3-diethylamino-1-phenyl-propyl)-1,3-oxazolidin-2-one fumarate (diastereomer A)

Yield: 28.9% (amorphous)

$^1$H-NMR (CD$_3$OD) δ:

1.30 (6H, t, J=8 Hz), 2.2–2.6 (2H, m), 2.9–3.4 (10H, m), 4.6–5.0 (2H, m), 6.64 (2H, s), 7.0–7.6 (9H, m).

EXAMPLE 18

5-(2-Bromophenyl)methyl-3-(3-diethylamino-1-phenyl-propyl)-1,3-oxazolidin-2-one fumarate (diastereomer B)

Yield: 37.4% (amorphous)

$^1$H-NMR (CD$_3$OD) δ:

1.28 (6H, t, J=8 Hz), 2.2–2.6 (2H, m), 2.8–3.4 (9H, m), 3.63 (1H, t, J=8 Hz), 6.62 (2H, s), 6.9–7.5 (9H, m).

EXAMPLE 19

5-(2-Bromophenyl)methyl-3-[1-(4-chrorophenyl)-3-morpholinopropyl]-1,3-oxazolidin-2-one fumarate (diastereomer A)

Yield: 22.8% (white powder)

m.p.: 150°–155° C.

IR (KBr) cm$^{-1}$:

3425, 1730, 1710, 1560, 1490, 1425, 1360, 1300, 1250, 1170, 1120, 1090, 980, 830, 755, 640.

$^1$H-NMR (CD$_3$OD) δ:

2.1–2.4 (2H, m), 2.5–2.9 (6H, m), 3.0–3.5 (4H, m), 3.7–3.9 (4H, m), 4.6–5.1 (2H, m), 6.60 (2H, s), 7.0–7.6 (8H, m).

EXAMPLE 20

5-(2-Bromophenyl)methyl-3-[1-(4-chlorophenyl)-3-morpholinopropyl]-1,3-oxazolidin-2-one fumarate (diastereomer B)

Yield: 40.5% (white powder)

m.p.: 168°–169° C.

IR (KBr) cm$^{-1}$:

3400, 1730, 1690, 1565, 1420, 1300, 1240, 1165, 1035, 975, 750, 630.

$^1$H-NMR (CD$_3$OD) δ:

2.1–2.4 (2H, m), 2.6–3.1 (9H, m), 3.5–3.9 (5H, m), 4.7–5.0 (2H, m), 6.64 (2H, s), 6.9–7.5 (8H, m).

EXAMPLE 21

5-(2-Bromophenyl)methyl-3-(1-phenyl-3-piperidinopropyl)-1,3-oxazolidin-2-one fumarate (diastereomer A)

Yield: 26.7% (white powder)

m.p.: 178°–180° C. (decomp.)

IR (KBr) cm$^{-1}$:

1720, 1565, 1420, 1360, 1300, 1270, 1245, 1175, 1020, 750.

$^1$H-NMR (CD$_3$OD) δ:

1.4–2.0 (6H, m), 2.0–2.6 (2H, m), 2.6–3.4 (10H, m), 4.5–5.2 (2H, m), 6.69 (2H, s), 6.9–7.5 (9H, m).

EXAMPLE 22

5-(2-Bromophenyl)methyl-3-(1-phenyl-3-piperidinopropyl)-1,3-oxazolidin-2-one fumarate (diastereomer B)

Yield: 27.6% (white powder)

m.p.: 155°–156° C. (decomp.)

IR (KBr) cm$^{-1}$:

1725, 1705, 1570, 1420, 1360, 1290, 1240, 1175, 1070, 1040, 1020, 980, 750, 745, 690, 625.

$^1$H-NMR (CD$_3$OD ) δ:

1.4–2.0 (6H, m), 2.0–2.6 (2H, m), 2.6–3.4 (9H, m), 3.4–3.7 (1H, m), 4.5–5.2 (2H, m), 6.68 (2H, s), 6.9–7.5 (9H, m).

EXAMPLE 23

5-(4-Chlorophenyl)methyl-3-(3-morpholino-1-phenyl-propyl)-1,3-oxazolidin-2-one fumarate (diastereomer A)

Yield: 9.8% (white powder)

m.p.: 165°–166° C. (decomp.)

IR (KBr) cm$^{-1}$:

1745, 1700, 1520, 1410, 1290, 1240, 1120, 1100, 760.

$^1$H-NMR (D$_2$O) δ:

2.2–2.4 (2H, m), 2.9–3.3 (6H, m), 3.4–3.6 (2H, m), 3.7–4.2 (6H, m), 5.0–5.1 (1H, m), 6.67 (1*H, s*), 7.3–7.5 (9H, m).

EXAMPLE 24

5-(4-Chlorophenyl)methyl-3-(3-morpholino-1-phenyl-propyl)-1,3-oxazolidin-2-one fumarate (diastereomer B)

Yield: 9.6% (amorphous)

IR (KBr) cm$^{-1}$:

1750, 1690, 1540, 1400, 1290, 1240, 980, 760.

$^1$H-NMR (CD$_3$OD) δ:

2.1–2.3 (2H, m), 2.7–3.1 (8H, m), 3.69 (1H, d, d, J=6 Hz, 10 Hz), 3.7–3.9 (4H, m), 4.01 (1H, d, d, J=6 Hz, 10 Hz), 6.72 (1H, s), 7.2–7.4 (9H, m).

EXAMPLE 25

5-[2-(2-bromophenyl)ethyl]-3-(3-morpholino-1-phenyl-propyl)-1,3-oxazolidin-2-one fumarate (diastereomer A)

Yield: 30.0% (amorphous)

IR (KBr) cm$^{-1}$:
3425, 1720, 1430, 1260, 980, 750, 700, 640.
$^1$H-NMR (CD$_3$OD) δ:
1.7–3.1 (10H, m), 3.1–3.3 (4H, m), 3.4–3.9 (4H, m), 4.3–4.6 (1H, m), 4.8–5.0 (1H, m), 6.64 (2H, s), 6.9–7.6 (9H, m).

EXAMPLE 26

5-[2-(2-Bromophenyl)ethyl]-3-(3-morpholino-1-phenylpropyl)-1,3-oxazolidin-2-one fumarate (diastereomer B)

Yield: 25.7% (amorphous)

IR (KBr) cm$^{-1}$:
3425, 2950, 1720, 1610, 1420, 1250, 1110, 980, 750, 700, 640.
$^1$H-NMR (CD$_3$OD) δ:
1.6–1.9 (2H, m), 2.1–2.5 (2H, m), 2.5–2.9 (9H, m), 3.5–3.9 (5H, m), 4.4–4.7 (1H, m), 4.8–5.1 (1H, m), 6.64 (2H, s), 6.9–7.5 (9H, m).

EXAMPLE 27

5-[2-(2-Chlorophenyl)ethyl]-3-(3-morpholino-1-phenylpropyl)-1,3-oxazotidin-2-one fumarate (diastereomer A)

Yield: 14.8% (amorphous)

IR (KBr) cm$^{-1}$:
3500, 2925, 1720, 1430, 1240, 1070, 1040, 970, 750, 690, 640.
$^1$H-NMR (CD$_3$OD) δ:
1.7–2.1 (2H, m), 2.2–2.5 (2H, m), 2.5–3.2 (10H, m), 3.7–3.9 (4H, m), 4.2–4.6 (1H, m), 4.8–5.1 (1H, m), 6.64 (2H, s), 7.0–7.4 (9H, m).

EXAMPLE 28

5-[2-(2-Chlorophenyl)ethyl]-3-(3-morpholino-1-phenylpropyl)-1,3-oxazolidin-2-one fumarate (diastereomer B)

Yield: 23.7% (amorphous)

IR (KBr) cm$^{-1}$:
3400, 2925, 1720, 1430, 1240, 1070, 1030, 970, 750, 690, 635.
$^1$H-NMR (CD$_3$OD) δ:
1.6–1.9 (2H, m), 2.1–2.5 (2H, m), 2.5–3.2 (9H, m), 3.5–3.9 (5H, m), 4.4–4.8 (1H, m), 4.8–5.1 (1H, m), 6.64 (2H, s), 7.0–7.4 (9H, m).

EXAMPLE 29

5-(2-Bromophenyl)methyl-3-(1-phenyl-3-pyrrolidinopropyl)-1,3-oxazolidin-2-one fumarate (diastereomer A)

Yield: 4.4% (white powder)

m.p.: 144°–149° C.

IR (KBr) cm$^{-1}$:
3400, 2950, 2600, 1730, 1250, 980, 760.
$^1$H-NMR (CD$_3$OD) δ:
2.1–3.4 (16H, m), 4.9–4.93 (2H, m), 6.71 (2H, s), 7.2–7.6 (9H, m).

EXAMPLE 30

5-(2-bromophenyl)methyl-3-(1-phenyl-3-pyrrolidinopropyl)-1,3-oxazolidin-2-one fumarate (diastereomer B)

Yield: 16.1% (pale yellow powder)

m.p.: 130°–132° C.

IR (KBr) cm$^{-1}$:
3400, 2940, 2600, 1740, 1260, 980, 750.
$^1$H-NMR (CD$_3$OD) δ:
2.1–2.5 and 3.1–3.4 (12H, m), 2.9–3.1 and 3.6–3.7 (4H, m), 4.9–5.0 (2H, m), 6.69 (2H, s), 7.1–7.5 (9H, m).

EXAMPLE 31

5-(3-Chlorophenyl)methyl-3-(3-morpholino-1-phenylpropyl)-1,3-oxazolidin-2-one fumarate (diastereomer A)

Yield: 16% (amorphous)

IR (KBr) cm$^{-1}$:
3400, 1730, 1425, 1365, 1250, 1080, 980, 760, 700, 645.
$^1$H-NMR (CD$_3$OD) δ:
2.0–2.5 (2H, m), 2.5–3.4 (8H, m), 3.6–4.1 (6H, m), 4.5–4.8 (1H, m), 6.73 (2H, s), 7.0–7.4 (9H, m).

EXAMPLE 32

5-(3-Chlorophenyl)methyl-3-(3-morpholino-1-phenylpropyl)-1,3-oxazolidin-2-one fumarate (diastereomer B)

Yield: 14.8% (white powder)

m.p.: 141°–143° C. (decomp.)

IR (KBr) cm$^{-1}$:
3430, 1735, 1420, 1300, 1240, 1075, 980.
$^1$H-NMR (D$_2$O) δ:
2.3–2.5 (4H, m), 2.70 (2H, d, d, J=4 Hz, 5 Hz), 2.9–4.3 (26H, m), 5.0–5.1 (2H, m), 6.67 (2H, s), 7.0–7.3 (3H, m), 7.30–7.5 (6H, m).

EXAMPLE 33

5-Benzyl-3-(3-morpholino-1-phenylpropyl)-1,3-oxazolidin-2-one fumarate (diastereomer B)

Yield: 25.1% m.p.: 164°–168° C. (decomp.)

IR (KBr) cm$^1$:
3420, 2920, 2600, 1725, 1675, 1610, 1450, 1425, 1250, 1070, 1040, 980, 750, 695.
$^1$H-NMR (CD$_3$OD) δ:
2.0–2.4 (2H, m), 2.6–3.4 (9H, m), 3.48 (1H, t, J=8 Hz), 3.6–3.9 (4H, m), 4.6–5.0 (2H, m), 6.71 (2H, s), 6.8–7.4 (10H, m).

EXAMPLE 34

5-(2-Bromophenyl)methyl-3-[1-(4-methylphenyl)-3-morpholinopropyl]-1,3-oxazolidin-2-one fumarate (diastereomer A)

Yield: 28.9% (amorphous product)

IR (KBr) cm$^{-1}$:
1730, 1640, 1580, 1470, 1420, 1365, 1245, 1130, 1080, 1020, 980, 750.
$^1$H-NMR (D$_2$O) δ:
2.33 (3H, s), 2.2–2.4 and 2.8–4.2 (16H, m), 4.6–5.2 (2H, m), 6.69 (2H, s), 7.2–7.8 (8H, m).

EXAMPLE 35

5-(2-Bromophenyl)methyl-3-[1-(4-methylphenyl)-3-morpholinopropyl]-1,3-oxazolidin-2-one fumarate (diastereomer B)

Yield: 26.9% (white powder)

m.p.: 152°–153° C. (decomp.)

IR (KBr) cm$^{-1}$:

1730, 1710, 1420, 1390, 1360, 1300, 1260, 1205, 1180, 1130, 1080, 1040, 765.
$^1$H-NMR (D$_2$O) δ:
2.38 (3H, s), 2.2–2.5 (2H, m), 3.0–3.7 (9H, m), 3.6–4.2 (4H, m), 3.7–3.8 (1H, m), 4.7–5.0 (1H, 6.58 (2H, s), 7.0–7.5 (8H, m).

EXAMPLE 36

5-(2-Bromophenyl)methyl-3-[1-phenyl-3-(4-thiomorpholinyl)propyl]-1,3-oxazolidin-2-one mesylate (diastereomer A)

Yield: 21.8% (white powder)
m.p.: 183–°185° C.
IR (KBr) cm$^{-1}$:
1745, 1430, 1260, 1220, 1150, 1060, 1035, 770, 740, 700, 560.
$^1$H-NMR (D$_2$O) δ:
2.1–2.4 (2H, m), 2.81 (3H, s), 2.8–3.1 (8H, m), 3.2–3.8 (8H, m), 4.9–5.0 (1H, m), 7.3–7.5 (8H, m), 7.73 (1H, d, J=8 Hz).

EXAMPLE 37

5-(2-Bromophenyl)methyl-3-[1-phenyl-3-(4-thiomorpholinyl)propyl]-1,3-oxazolidin-2-one mesylate (diastereomer B)

Yield: 20.0% (amorphous)
IR (KBr) cm$^{-1}$:
3420, 1730, 1470, 1420, 1235, 1200, 1190, 1055, 1030, 780, 755, 695.
$^1$H-NMR (D$_2$O) δ:
2.4–2.5 (2H, m), 2.83 (3H, s), 3.6–3.9 (2H, m), 6.7–7.4 (9H, m).

EXAMPLE 38

5-(3-Methylphenyl)methyl-3-(3-morpholino-1-phenylpropyl)-1,3-oxazolidin-2-one fumarate (diastereomer A)

Yield: 22.1% (amorphous)
IR (KBr) cm$^{-1}$:
1730, 1485, 1420, 1370, 1240, 1070, 1020, 980, 970, 780, 780, 750, 690.
$^1$H-NMR (D$_2$O) δ:
1.9–4.3 (16H, m), 2.32 and 2.35 (3H, s), 4.6–5.1 (2H, m), 6.67 (2H, s), 7.1–7.6 (9H, m).

EXMPALE 39

5-(3-Methylphenyl)methyl-3-(3-morpholino-1-phenylpropyl)-1,3-oxazolidin-2-one fumarate (diastereomer B)

Yield: 18.4% (white powder)
m.p.: 142°–143° C. (decomp.)
IR (KBr) cm$^{-1}$:
1730, 1705, 1570, 1420, 1405, 1370, 1300, 1260, 1240, 1175, 1075, 790, 750, 630.
$^1$H-NMR (D$_2$O) δ:
2.22 (3H, s), 2.3–2.5 (2H, m), 2.0–3.6 (9H, m), 3.6–3.8 (1H, m), 3.8–4.2 (4H, m), 4.6–4.9 (1H, m), 4.9–5.1 (1H, m), 6.57 (2H, s), 6.8–7.5 (9H, m).

EXAMPLE 40

3-(3-Morpholino-1-phenylpropyl)-5-phenyl-1,3-oxazolidin-2-one fumarate (diastereomer B)

Yield: 9.9% (pale yellow amorphous product)
IR (KBr) cm$^{-1}$:
3420, 1730, 1230, 980, 690.
$^1$H-NMR (CD$_3$OD) δ:
2.4–3.1 (8H, m), 3.6–4.1 (6H, m), 5.0–5.1 (1H, m), 5.5–5.6 (1H, m), 6.72 (2H, s), 7.1–7.4 (10H, m).

EXAMPLE 41

5-(2-Bromophenyl)methyl-3-[3-(4-hydroxypiperidino)-1-phenylpropyl)-1,3-oxazolidin-2-one fumarate (diastereomer B)

Yield: 45.0% (amorphous)
IR (KBr) cm$^{-1}$:
3400, 1730, 1570, 1430, 1370, 1250, 1040, 980, 760.
$^1$H-NMR (CD$_3$OD) δ:
1.7–2.1 (4H, m), 2.3–2.6 (2H, m), 2.8–3.5 (9H, m), 3.6–3.7 (1H, m), 3.8–4.0 (1H, m), 6.69 (2H, s), 7.0–7.5 (9H, m).

EXAMPLE 42

5-(2-Bromophenyl)methyl-3-[3-(4-methoxypiperidino)-1-phenylpropyl)-1,3-oxazolidin-2-one fumarate (diastereomer A)

Yield: 42.0% (amorphous)
IR (KBr) cm$^{-1}$:
3420, 2940, 1740, 1430, 1365, 1250, 1105, 1080, 1025, 985, 760, 700, 645.
$^1$H-NMR (D$_2$O) δ:
1.6–1.8 (1H, m), 1.8–2.0 (1H, m), 2.1–2.4 (4H, m), 2.6–3.8 (1H, m), 3.41 (3H, s), 6.67 (2H, s), 7.2–7.5 (8H, m), 7.7 (1H, d, J=8 Hz).

EXAMPLE 43

5-(2-Bromophenyl)methyl-3-[3-(4-methoxypiperidino)-1-phenylpropyl)-1,3-oxazolidin-2-one fumarate (diastereomer B)

Yield: 43.0% (amorphous)
IR (KBr) cm$^{-1}$:
3430, 2980, 1740, 1470, 1425, 1360, 1240, 1100, 1075, 1025, 980, 755, 700, 640.
$^1$H-NMR (CD$_3$OD) δ:
1.8–2.2 (4H, m), 2.3–2.6 (2H, m), 2.8–3.8 (11H, m), 3.35 (3H, s), 6.69 (2H, s), 7.0–7.6 (9H, m).

EXAMPLE 44

5-(2-Bromophenyl)methyl-3-(3-morpholino-1-phenylpropyl)-1,3-oxazolidin-2-thione mesylate (diastereomer A)

Yield: 28.0% (white powder)
m.p.: 184°–185° C. (decomp.)
IR (KBr) cm$^{-1}$:
1485, 1445, 1310, 1235, 1215, 1150, 1130, 1120, 1020, 760, 755.
$^1$H-NMR (CD$_3$OD) δ:
2.4–2.6 (2H, m), 2.71 (3H, s), 3.0–4.2 (14H, m), 4.9–5.1 (1H, m), 5.8–5.9 (1H, m), 7.1–7.3 (1H, m) 7.3–7.7 (8H, m).

EXAMPLE 45

5-(2-Bromophenyl)methyl-3-(3-morpholino-1-phenylpropyl)-1,3-oxazolidin-2-thione mesylate (diastereomer B)

Yield: 24.3% (white powder)

m.p.: 179°–180° C. (decomp.)

IR (KBr) cm$^{-1}$:

1485, 1440, 1320, 1220, 1190, 1160, 1150, 1130, 1015, 750, 550.

$^1$H-NMR (CD$_3$OD) δ:

2.4–2.6 (2H, m), 2.7 (3H, s), 2.9–4.1 (14H, m), 5.1–5.2 (1H, m), 5.8–5.9 (1H, m), 7.0–7.5 (9H,

EXAMPLE 46

5-(1-Naphthyl)methyl-3-(3-morpholino-1-phenylpropyl)-1,3-oxazolidin-2-one mesylate (diastereomer A)

Yield: 37.3% (amorphous)

IR (KBr) cm$^{-1}$:

3430, 2960, 2870, 1740, 1250, 980, 780, 700.

$^1$H-NMR (CD$_3$OD) δ:

2.1–2.9 (8H, m), 3.2–3.8 (8H, m), 4.8–5.0 (2H, m), 6.72 (2H, s), 7.3–8.1 (12H, m).

EXAMPLE 47

5-(1-Naphthyl)methyl-3-(3-morpholino-1-phenylpropyl)-1,3-oxazolidin-2-one mesylate (diastereomer B)

Yield: 24.3% (amorphous)

IR (KBr) cm$^{-1}$:

3430, 2960, 2870, 1730, 1250, 980, 780, 700.

$^1$H-NMR (CD$_3$OD) δ:

2.0–3.9 (16H, m), 4.7–5.0 (2H, m), 6.70 (2H, s), 7.1–7.9 (12H, m).

EXAMPLE 48

5-(4-Fluorophenyl)methyl-3-(3-morpholino-1-phenylpropyl)-1,3-oxazolidin-2-one fumarate (diastereomer A)

Yield: 16.9% (white powder)

IR (KBr) cm$^{-1}$:

2850, 2420, 1740, 1720, 1570, 1450, 1430, 1305, 1270, 1180, 1120, 1045, 990, 750, 640.

$^1$H-NMR (CD$_3$OD) δ:

2.1–2.3 (2H, m), 2.5–2.7 (3H, m), 2.8–3.4 (8H, m), 3.8–3.9 (4H, m), 4.7–4.9 (2H, m), 6.73 (2H, s) 7.0–7.4 (9H, m).

EXAMPLE 49

5-(4-Fluorophenyl)methyl-3-(3-morpholino-1-phenylpropyl)-1,3-oxazolidin-2-one fumarate (diastereomer B)

Yield: 38.3% (white powder)

m.p.: 157°–59° C. (decomp.)

IR (KBr) cm$^{-1}$:

2950, 2430, 1740, 1730, 1580, 1510, 1430, 1305, 1250, 1225, 1180, 850, 760, 640.

$^1$H-NMR (CD$_3$OD) δ:

2.1–2.4 (2H, m), 2.7–3.1 (9H, m), 3.61 (1H, t, J=9 Hz), 3.7–3.9 (4H, m), 4.7–5.0 (2H, m), 6.72 (2H, s), 6.8–7.4 (9H, m).

EXAMPLE 50

3-(3-Morpholino-1-phenylpropyl)-5-(2-phenylethyl)-1,3-oxazolidin-2-one fumarate (diastereomer A)

Yield: 10.4% (white powder)

m.p.: 168.5°–170° C. (decomp.)

IR (KBr) cm$^{-1}$:

2950, 2450, 1745, 1450, 1420, 1395, 1270, 1245, 1210, 1145, 1090, 990, 760, 700, 635, 460.

$^1$H-NMR (CD$_3$OD) δ:

1.9–2.1 (2H, m), 2.2–2.5 (2H, m), 2.6–3.0 (8H, m), 3.2–3.4 (2H, m), 3.7–3.9 (4H, m), 4.45 (1H, m), 4.96 (1H, m), 6.72 (2H, s), 7.1–7.5 (10H, m).

EXAMPLE 51

3-(3-Morpholino-1-phenylpropyl)-5-(2-Phenylethyl)-1,3-oxazolidin-2-one fumarate (diastereomer B)

Yield: 14.4% (white powder)

m.p.: 142°–143° C. (decomp.)

IR (KBr) cm$^{-1}$:

2950, 2450, 1740, 1420, 1400, 1260, 1240, 1140, 1090, 1050, 1020, 750, 700, 640, 446.

$^1$H-NMR (CD$_3$OD) δ:

1.7–1.9 (2H, m), 2.2–2.5 (2H, m), 2.5–2.7 (2H, m), 2.7–3.0 (7H, m), 3.65 (1H, t, J=9 Hz), 3.7–3.9 (4H, m), 4.55 (1H, m), 5.00 (1H, m), 6.72 (2H, s), 7.0–7.5 (10H, m).

EXAMPLE 52

5-(2-Bromophenyl)methyl-3-[3-(hexahydro-1,4-oxazepin-4-yl)-1-phenylpropyl]-1,3-oxazolidin-2-one fumarate (diastereomer A)

Yield: 16.4% (white powder)

m.p.: 145°–147° C.

IR (KBr) cm$^{-1}$:

3400, 2950, 1730, 1420, 1250, 1130, 1070, 1020, 980, 920, 760, 695, 640.

$^1$H-NMR (CD$_3$OD) δ:

2.1–2.2 (2H, m), 2.3–2.5 (2H, m), 3.0–3.5 (10H, m), 3.8–3.9 (4H, 4.8–5.6 (2H, m), 6.76 (2H, s), 7.1–7.7 (9H, m).

EXAMPLE 53

5-(2-Bromophenyl)methyl-3-[3-(hexahydro-1,4-oxazepin-4-yl)-1-phenylpropyl]-1,3-oxazolidin-2-one fumarate (diastereomer B)

Yield: 20.5% (amorphous)

IR (KBr) cm$^{-1}$:

3400, 2925, 1730, 1425, 1370, 1240, 1135, 980, 750, 695, 640.

$^1$H-NMR (CD$_3$OD) δ:

2.1–2.2 (2H, m), 2.5–2.8 (2H, m), 2.9–3.5 (9H, m), 3.62 (1H, t, J=8 Hz), 4.9–5.0 (2H, m), 6.70 (2H, s), 7.1–7.5 (9H, m).

EXAMPLE 54

5-(4-Methoxyphenyl)methyl-3-(3-morpholino-1-phenylpropyl)-1,3-oxazolidin-2-one fumarate Yield: 5.6% (amorphous)

IR (KBr) cm$^{-1}$:

3440, 2930, 1730, 1620, 1520, 1250, 990, 650.

$^1$H-NMR (CD$_3$OD) δ:

2.2–3.0 (10H, m), 3.0–3.8 (6H, m), 3.76 (3H, s), 4.7–4.9 (2H, m), 6.71 (2H, s), 6.7–7.3 (9H, m).

EXAMPLE 55

3-(3-Morpholino-1-phenylpropyl)-5-(2-thenyl)-1,3-oxazolidin-2-one fumarate (diastereomer A)

Yield: 19.7% (white powder)

m.p. 141°–146 ° C. (decomp.)

IR (KBr) cm$^{-1}$:

3400, 1720, 1650, 1565, 1490, 1430, 1365, 1305, 1250, 1180, 1125, 1095, 920, 790, 755, 725, 695.

$^1$H-NMR (CD$_3$OD) δ:

2.1–2.2 (2H, m), 2.3–2.9 (6H, m), 3.1–3.3 (4H, m), 3.7–3.8 (4H, m), 4.7–4.9 (2H, m), 6.72 (2H, s), 6.9–7.4 (8H, m).

EXAMPLE 56

3-(3-Morpholino-1-phenylpropyl)-5-(2-thenyl)-1,3-oxazolidin-2-one fumarate (diastereomer B)

Yield: 16.1% (white powder)

m.p.: 160°–165° C. (decomp.)

IR (KBr) cm$^{-1}$:

3400, 1730, 1650, 1570, 1425, 1365, 1290, 1245, 1070, 1035, 980, 790, 750, 690, 630.

$^1$H-NMR (CD$_3$OD) δ:

2.2–2.4 (2H, m), 2.8–3.2 (9H, m), 3.5–3.6 (1H, m), 3.7–3.9 (4H, m), 4.8–4.9 (2H, m), 6.72 (2H, s), 6.8–7.4 (8H, m).

EXAMPLE 57

3-(3-Morpholino-1-phenylpropyl)-5-(3-phenylpropyl)-1,3-oxazolidin-2-one fumarate (diastereomer A)

Yield: 31% (white powder)

m.p.: 165°–167 ° C.

IR (KBr) cm$^{-1}$:

3420, 1720, 1445, 1425, 1255, 695.

$^1$H-NMR (CD$_3$OD) δ:

1.6–1.8 (4H, m), 2.2–2.4 (2H, m), 2.6–2.8 (8H, m), 3.1–3.3 (2H, m), 3.7–3.8 (4H, m), 4.4–4.5 (1H, m), 4.9–5.0 (1H, m), 6.73 (2H, s), 7.1–7.4 (10H, m).

EXAMPLE 58

3-(3-Morpholino-1-phenylpropyl)-5-(3-phenylpropyl)-1,3-oxazolidin-2-one fumarate (diastereomer B)

Yield: 42% (amorphous)

IR (KBr) cm$^{-1}$:

3420, 2920, 1730, 1440, 1420, 1370, 1240, 980, 695.

$^1$H-NMR (CD$_3$OD) δ:

1.4–1.6 (4H, m), 2.3–2.6 (4H, m), 2.6–2.8 (1H, m), 2.8–3.2 (6H, m), 3.6–3.7 (1H, m), 3.8–3.9 (4H, m), 4.5–4.6 (1H, m), 4.9–5.0 (1H, m), 6.72 (2H, s), 7.0–7.4 (10H, m).

EXAMPLE 59

3-[3-(4-Acetylpiperazinyl)-1-phenylpropyl]-5-benzyl-1,3-oxazolidin-2-one (diastereomer A)

m.p.: oil $^1$H-NMR (CDCl$_3$) δ:

2.08 (3H, s), 2.1–2.3 (2H, m), 2.3–2.5 (6H, m), 2.9–3.1 (2H, m), 3.1–3.2 (2H, m), 3.4–3.5 (2H, m), 3.6–3.7 (2H, m), 4.6–4.7 (1H, m), 5.0–5.1 (1H, m), 7.1–7.3 (10H, m).

EXAMPLE 60

3-[3-(4-Acetylpiperazinyl)-1-phenylpropyl]-5-benzyl-1,3-oxazolidin-2-one (diastereomer B)

m.p.: oil $^1$H-NMR (CDCl$_3$) δ:

2.07 (3H, s), 2.1–2.2 (2H, m), 2.3–2.5 (6H, m), 2.7–2.75 (1H, m), 2.8–3.0 (2H, m), 3.4–3.45 (1H, m), 3.4–3.5 (2H, m), 3.55–3.6 (2H, m), 4.6–4.7 (1H, m), 5.0–5.1 (1H, m), 7.1–7.3 (10H, m).

EXAMPLE 61

5-Benzyl-3-[3-morpholino-1-(2-thienyl)propyl]-1,3-oxazolidin-2-one (diastereomer A)

m.p.: 143°–145° C.

IR (KBr) cm$^{-1}$:

3400, 1715, 1560, 1480, 1420, 1360, 1300, 1250, 1180, 1120, 1090, 1005, 990, 910, 840, 790, 750, 695, 640.

$^1$H-NMR (DMSO-d$_6$) δ:

1.8–2.0 (1H, m), 2.0–2.1 (1H, m), 2.1–2.2 (2H, m), 2.3–2.4 (4H, m), 2.9–3.0 (2H, m), 3.2–3.7 (6H, m), 4.7–4.8 (1H, m), 5.0–5.1 (1H, m), 6.60 (2H, s), 7.0–7.1 (2H, m), 7.2–7.5 (6H, m).

EXAMPLE 62

5-Benzyl-3-[3-morpholino-1-(2-thienyl)propyl]-1,3-oxazolidin-2-one (diastereomer B)

m.p.: 135°–136° C.

IR (KBr) cm$^{-1}$:

3400, 1730, 1420, 1360, 1290, 1240, 1170, 1080, 1040, 980, 790, 750, 690, 640.

$^1$H-NMR (CDCl$_3$) δ:

2.0–2.1 (2H, m), 2.2–2.4 (6H, m), 2.8–3.0 (2H, m), 3.4–3.6 (6H, m), 4.7–4.8 (1H, m), 5.0–5.1 (1H, m), 6.60 (2H, s), 6.9–7.0 (2H, m), 7.1–7.5 (6H, m).

EXAMPLE 63

5-Benzyl-3-(morpholino-1-phenylpropyl]-1,3-thiazolidin-2-one fumarate (diastereomer A)

m.p.: 150°–155° C.

IR (KBr) cm$^{-1}$:

3400, 1700, 1640, 1440, 1395, 1290, 1250, 1165, 1070, 985, 740, 690, 630.

$^1$H-NMR (CD$_3$OD) δ:

2.3–2.4 (2H, m), 2.7–3.5 (10H, m), 3.8–3.9 (4H, m), 3.9–4.6 (1H, m), 5.2–5.3 (1H, m), 6.75 (2H, s), 7.2–7.4 (10H, m).

EXAMPLE 64

5-Benzyl-3-(morpholino-1-phenylpropyl]-1,3-thiazolidin-2-one fumarate (diastereomer B)

m.p.: 148°–150° C.

IR (KBr) cm$^{-1}$:

3400, 1695, 1650, 1395, 1260, 1200, 1120, 1070, 970, 740, 685, 620.

$^1$H-NMR (CD$_3$OD) δ:

2.2–2.3 (2H, m), 2.5–3.1 (9H, m), 3.6–3.7 (1H, m), 3.7–3.9 (5H, m), 5.3–5.4 (1H, m), 6.72 (2H, s), 7.1–7.5 (10H, m).

EXAMPLE 65

3-(3-Morpholino-1-phenylpropyl)-1,3-oxazolidin-2-one fumarate m.p.: amorphous
IR (KBr) cm$^{-1}$:
3420, 1730, 1420, 1250, 1070, 1040, 980, 760, 695, 640.
$^1$H-NMR (D$_2$O) δ:
2.4–2.6 (2H, m), 3.1–3.7 (8H, m), 3.8–4.2 (4H, m), 4.3–4.5 (2H, m), 4.96 (1H, t, J=8 Hz), 6.69 (2H, s), 7.4–7.6 (5H, m).

EXAMPLE 66

5-Methyl-3-(3-morpholino-1-phenylpropyl)-1,3-oxazolidin-2-one fumarate (mixture of diastereomers)

m.p.: amorphous
IR (KBr) cm$^{-1}$:
3400, 2955, 1720, 1630, 1560, 1480, 1420, 1360, 1240, 1120, 970, 905, 865, 790, 750, 690, 640, 540.
$^1$H-NMR (DMSO-d$_6$) δ:
1.1–1.3 (3H, m), 2.0–2.2 (2H, m), 2.2–2.6 (6H, m), 3.1–3.2 (1H, m), 3.27–3.33 (1H, m), 3.5–3.7 (4H, m), 4.5–4.6 (1H, m), 4.8–4.9 (1H, m), 6.60 (2H, s), 7.2–7.4 (5H, m).

EXAMPLE 67

4-Isobutyl-3-(3-morpholino-1-phenylpropyl)-1,3-oxazolidin-2-one fumarate (mixture of diastereomers A & B; A/B=10/6)

m.p.: 133°–143° C. (decomp.)
IR (KBr) cm$^{-1}$:
3420, 2950, 1750, 1580, 1420, 1260, 1170, 1130, 1070, 980, 790, 760, 700, 630.
$^1$H-NMR (CD$_3$OD) δ:
0.6–0.9 (9.6H, m), 1.2–1.7 (4.8H, m), 2.3–3.0 (3.2H, m), 2.9–3.1 (9.6H, m), 3.5–3.8 (9.6H, m), 3.8–3.9 (6.4H, m), 3.9–4.0, 4.3–4.4 (3.2H, m), 4.5–4.7, 4.8–4.9 (1.6H, m), 6.72 (3.2H, s), 7.3–7.5 (8H, m).

EXAMPLE 68

3-(3-Morpholino-1-phenylpropyl)-4-phenyl-1,3-oxazolidin-2-one fumarate (diastereomer A)

m.p.: 155°–167° C. (decomp.)
IR (KBr) cm$^{-1}$:
3400, 1735, 1720, 1425, 1075, 695.
$^1$H-NMR (CD$_3$OD) δ:
1.9–2.1 (2H, m), 2.6–2.9 (6H, m), 3.7–3.8 (4H, m), 4.16 (1H, dd, J=6 Hz, 8 Hz), 4.4–4.6 (2H, m), 4.97 (1H, dd, J=7 Hz, 8 Hz), 6.71 (2H, s), 7.1–7.5 (10H, m).

EXAMPLE 69

4-Benzyl-3-(3-morpholino-1-phenylpropyl)-1,3-oxazolidin-2-one fumarate (diastereomer A)

m.p.: 170°–172° C.
IR (KBr) cm$^{-1}$:
3430, 1745, 1720, 1425, 1305, 1260, 1250.
$^1$H-NMR (CD$_3$OD) δ:
2.3–2.5 (1H, m), 2.6–2.7 (2H, m), 2.8–3.0 (6H, m), 3.20 (1H, dd, J=4 Hz, 13 Hz), 3.7–3.9 (5H, m), 4.04 (2H, d, J=7 Hz), 4.97 (1H, dd, J=6 Hz, 8 Hz), 6.72 (2H, s), 6.9–7.0 (2H, m), 7.1–7.3 (3H, m), 7.4–7.6 (5H, m).

EXAMPLE 70

2-(2-Bromobenzyl)-4-(3-morpholino-1-phenylpropyl)-5-morpholinone fumarate (diastereomer A)

m.p.: amorphous
IR (KBr) cm$^{-1}$:
3400, 1700, 1640, 1425, 1270, 1130, 1070, 750, 690, 640.
$^1$H-NMR (CD$_3$OD) δ:
2.3–2.5 (2H, m), 2.8–3.3 (8H, m), 3.3–3.4 (2H, m), 3.8–4.0 (4H, m), 4.1–4.3 (2H, m), 4.8–4.9 (1H, m), 6.8–6.9 (1H, m), 6.73 (2H, s), 7.1–7.6 (9H, m).

2-(2-Bromobenzyl)-5-morpholinone (from which the above fumarate was prepared)

IR (KBr) cm$^{-1}$:
3200, 3050, 1685, 1490, 1460, 1420, 1100, 1035, 1015, 900, 820, 750, 730, 450.
$^1$H-NMR (CD$_3$OD) δ:
2.9–3.1 (2H, m), 3.2–3.3 (1H, m), 3.3–3.4 (1H, m), 3.9–4.0 (1H, m), 4.10 (1H, d, J=4 Hz), 4.26 (1H, d, J=4 Hz), 6.71 (1H, broad s), 7.1–7.6 (4H, m).

EXAMPLE 71

2-(2-Bromobenzyl)-4-(3-morpholino-1-phenylpropyl)-5-morpholinone fumarate (diastereomer B)

m.p.: 103° C.
IR (KBr) cm$^{-1}$:
3450, 1640, 1440, 1350, 1270, 1120, 1090, 1070, 1040, 980, 755, 700, 640.
$^1$H-NMR (CD$_3$OD) δ:
2.2–2.4 (2H, m), 2.7–3.0 (8H, m), 3.3–3.4 (2H, m), 3.7–3.9 (4H, m), 4.1–4.3 (2H, m), 4.8–4.9 (1H, m), 6.8–6.9 (1H, m), 6.74 (2H, s), 7.1–7.6 (9H, m).

EXAMPLES 72 & 73

5-Benzyl-4-(3-morpholino-1-phenylpropyl)-3-morpholinone

To a suspension of 60% NaH (80 mg, 2 mmol) in dry dimethylformamide (8 ml) was added 5-benzyl-3-morpholinone (880 mg, 2 mmol). The mixture was stirred at room temperature for 1 hour. To this were added 4-(3-chloro-3-phenylpropyl)morpholine (480 mg, 2 mmol) and dry dimethylforamide (1 ml). The mixture was then stirred overnight at 60° C. The stirred mixture was placed under reduced pressure to evaporate the solvent. Water was added to the residue, and extraction with ethyl acetate was performed. The extract was washed with a saturated aqueous brine and dried over anhydrous sodium sulfate. The dried extract was placed under reduced pressure to remove the solvent. The oily residue was placed on silica gel column and eluated with ethyl acetate/methanol (20/1) to yield the desired diastereomer A (168 mg, 21.3) and diastereomer B (156 mg, 19.8%).

5-Benzyl-3-morpholinone
$^1$H-NMR (CDCl$_3$) δ:
2.6–2.7 (1H, m), 2.8–2.9 (1H, m), 3.5–3.6 (1H, m), 3.7–3.8 (1H, m), 3.8–3.9 (1H, m), 4.1–4.27 (2H, m), 6.1 (1H, broad s), 7.1–7.4 (5H, m, aryl H).

Diastereomer A (Example 72)
$^1$H-NMR (CDCl$_3$) δ:
2.3–2.5 (8H, m), 3.0–3.2 (4H, m), 3.5–3.7 (1H, m), 3.6–3.8 (4H, m), 4.20 (1H, d, J=7 Hz), 4.35 (1H, d, J=7 Hz), 5.7–5.8 (1H, m), 7.0–7.4 (10H, m).

Diastereomer A (Example 73)

¹H-NMR (CDCl₃) δ:
2.3–2.5 (8H, m), 2.62–2.75 (1H, m), 3.5–3.7 (2H, m), 3.6–3.8 (6H, m), 4.20 (1H, d, J=6 Hz), 4.35 (1H, d, J=6 Hz), 5.75–5.85 (1H, m), 6.8–7.0 (2H, m), 7.1–7.6 (8H, m).

EXAMPLE 74

5-Benzyl-4-(3-morpholino-1-phenylpropyl)-3-morpholinone fumarate (diastereomer A)

m.p.: 173°–175° C.

IR (KBr) cm⁻¹:
3400, 1700, 1640, 1440, 1300, 1160, 1120, 1085, 980, 870, 790, 745, 690, 630.

¹H-NMR (CD₃OD) δ:
2.5–2.7 (2H, m), 2.8–3.2 (10H, m), 3.50 (1H, d, J=12 Hz), 3.8–3.9 (1H, m), 4.20 (1H, d, J=17 Hz), 4.34 (1H, d, J=17 Hz), 5.5–5.7 (1H, m), 6.71 (2H, s), 7.0–7.6 (10H, m).

EXAMPLE 75

5-Benzyl-4-(3-morpholino-1-phenylpropyl)-3-morpholinone fumarate (diastereomer B)

m.p.: 168°–176° C.

IR (KBr) cm⁻¹:
3400, 1710, 1630, 1440, 1420, 1290, 1250, 1160, 1120, 1090, 1065, 970, 900, 860, 745, 690, 630.

¹H-NMR (CD₃OD) δ:
2.4–2.6 (2H, m), 2.6–2.9 (8H, m), 3.5–3.6 (2H, m), 3.65 (1H, d, J=12 Hz), 3.7–3.9 (4H, m), 4.21 (1H, d, J=17 Hz), 4.32 (1H, d, J=17 Hz), 5.5–5.6 (1H, m), 6.72 (2H, s), 7.9–7.6 (10H, m).

EXAMPLE 76

3-(3-Morpholino-1-phenylpropyl)-4-phenethyl-1,3-oxazolidin-2-on fumarate (mixture of diastereomers A & B, A/B=10/4)

m.p.: amorphous

IR (KBr) cm⁻¹:
3410, 2910, 2500, 1720, 1380, 1240, 980, 750, 700, 640.

¹H-NMR (CD₃OD) δ:
1.5–2.1 (2.8H, m), 2.3–3.1 (14H, m), 3.5–3.9 (7H, m), 4.09 (1.4H, dd, J=6 Hz & 9 Hz), 4.33 (1H, dd, J=9 Hz & 9 Hz), 4.37 (0.4H, dd, J=9 Hz & 9 Hz), 4.69 (0.4H, dd, J=6 Hz & 10 Hz) 6.72 (2H, s), 6.9–7.6 (14H, m).

EXAMPLE 77

3-(3-Morpholino-1-phenylpropyl)-4-(1-naphthylmethyl)-1,3-oxazolidin-2-one fumarate (mixture of diastereomers A & B, A/B=10/3)

m.p.: 205°–208° C. (decomp.)

IR (KBr) cm⁻¹:
3400, 1725, 1550, 1440, 1395, 1240, 1160, 1120, 1065, 1020, 970, 865, 780, 750, 690, 630.

¹H-NMR (CD₃OD) δ:
2.4–3.1 (10H, m), 3.6–3.9 (6H, m), 4.5–4.6 (0.2H, m), 5.1–5.2 (0.8H, m), 6.71 (2H, s), 7.1–7.9 (12H, m).

EXMPALE 78

5-(3-Indolylmethyl)-3-(3-morpholino-1-phenylpropyl)-1,3-oxazolidin-2-one fumarate (diastereomer A)

m.p.: amorphous

IR (KBr) cm⁻¹:
3350, 1720, 1570, 1425, 1360, 1250, 980, 740, 700, 640.

¹H-NMR (D₂O) δ:
2.0–2.5 (2H, m), 2.9–3.6 (9H, m), 3.64 (1H, dd, J=9 Hz & 9 Hz), 3.6–4.2 (4H, m), 4.56 (1H, m), 5.06 (1H, m), 6.67 (2H, s), 6.8–6.9 (2H, m), 6.93 (1H, s), 7.09 (1H, dd, J=7 Hz & 8 Hz), 7.2–7.4 (4H, m), 7.45 (1H, d, J=8 Hz), 7.52 (1H, d, J=8Hz).

EXAMPLE 79

5-(3-Indolylmethyl)-3-(3-morpholino-1-phenylpropyl)-1,3-oxazolidin-2-one fumarate (diastereomer B)

m.p.: amorphous

IR (KBr) cm⁻¹:
3300, 1720, 1570, 1420, 1360, 1240, 980, 740, 700, 640.

¹H-NMR (D₂O) δ:
1.69 (1H, m), 1.8–2.0 (2H, m), 2.3–2.5 (2H, m), 2.6–3.4 (7H, m), 3.6–4.2 (4H, m), 5.00 (1H, 6.66 (2H, s), 7.2–7.5 (8H, m), 7.56 (1H, d, J=8 Hz), 7.78 (1H, d, J=8Hz).

EXAMPLE 80

4-(2-Bromobenzyl)-3-(3-morpholino-1-phenylpropyl)-1,3-oxazolidin-2-one fumarate (diastereomer A)

IR (KBr) cm⁻¹:
3420, 2910, 1740, 1430, 1400, 1240, 1070, 980, 750, 700, 640.

¹H-NMR (DMSO-d₆) δ:
2.1–2.5 (8H, m), 2.7–3.3 (2H, m), 3.5–3.7 (4H, m), 3.9–4.1 (3H, m), 4.7–4.9 (1H, m), 6.33 (2H, s), 7.1–7.6 (9H, m).

EXAMPLE 81

Preparation Example (Tablet)

Each tablet (100 mg) contained the following components:

| | |
|---|---|
| Effective ingredient (Alkylenediamine derivative of the invention) | 10 mg |
| Lactose | 55 |
| Crystalline cellulose | 20 |
| Carboxymethylcellulose calcium | 10 |
| Hydroxypropylcellulose | 4 |
| Magnesium stearate | 1 |

EXAMPLE 82

Preparation Example (Granules)

Each granule (1 g) contained the following components:

| | |
|---|---|
| Effective ingredinent (Alkylenediamine derivative of the invention) | 100 mg |
| Lactose | 450 |
| Corn starch | 400 |
| Hydroxypropylcellulose | 50 |

We claim:

1. An alkylenediamine derivative represented by the formula (1) or (2):

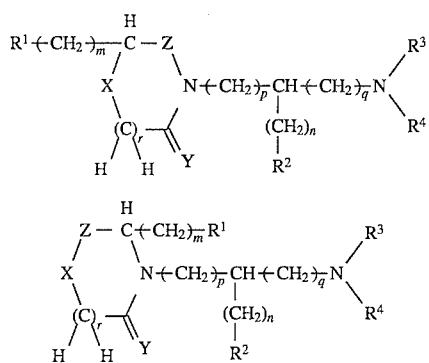

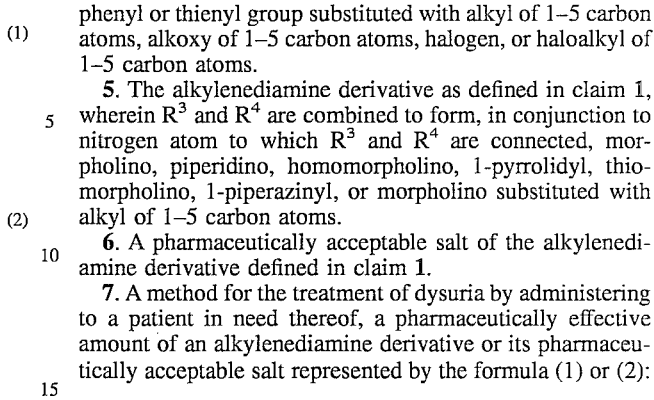

wherein

R¹ represents a phenyl, naphthyl or aromatic heterocyclic group each of which is unsubstituted or substituted with the same or different 1 to 5 substituent groups selected from those consisting of alkyl groups, halogen atoms, haloalkyl groups, hydroxyl group, alkoxyl groups, aryloxy groups, aralkyloxy groups, nitro group, amino group, cyano group, alkylamino groups, aralkylamino groups, arylamino groups, acylamino groups, carboxyl group, alkoxycarbonyl groups, aralkyloxycarbonyl groups, aryloxycarbonyl groups, carbamoyl group, sulfo group, alkoxysulfonyl groups, aralkyloxysulfonyl groups, aryloxysulfonyl groups, sulfonamide group and 1H-tetrazol-5-yl group; R² represents a phenyl, naphthyl or aromatic heterocyclic group each of which is unsubstituted or substituted with the same or different 1 to 5 substituent groups selected from those consisting of alkyl groups, halogen atoms, haloalkyl groups, hydroxyl group, alkoxyl groups, aryloxy groups, aralkyloxy groups, nitro group, amino group, cyano group, alkylamino groups, aralkylamino groups, arylamino groups, acylamino groups, carboxyl groups, alkoxy carbonyl groups, aralkyloxycarbonyl groups, aryloxycarbonyl groups, carbamoyl group, sulfo group, alkoxysulfonyl groups, aralkyloxysulfonyl groups, aryloxysulfonyl groups, sulfonamide group and 1H-tetrazol-5-yl group; each of R³ and R⁴ independently represents hydrogen atom, an alkyl group, an aralkyl group or an aryl group, or R³ and R⁴ are combined to form one of 5- to 7-membered cyclic groups which may contain oxygen atom, sulfur atom or nitrogen atom besides the nitrogen atom connected to both of R³ and R⁴ and each of which is unsubstituted or substituted with the same or different 1–5 substituent groups selected from those consisting of alkyl groups, aralkyl groups, phenyl group, hydroxyl group, alkoxyl groups, carboxyl group, alkoxycarbonyl groups, aralkyloxycarbonyl groups, aryloxycarbonyl groups, acyl groups and carbamoyl group; X represents oxygen atom, sulfur atom or imino group; Y represents oxygen atom or sulfur atom; Z represents —CH₂—, —CO— or —CS—; m is an integer of 0–4; n is an integer of 0–4; r is 0; and each of p and q independently represents an integer of 0–5 provided that p plus q is 1–5.

2. The alkylenediamine derivative as defined in claim 1, wherein X, Y and Z in the formula (1) or (2) represent oxygen atom, oxygen atom and —CH₂—, respectively.

3. The alkylenediamine derivative as defined in claim 1, wherein R¹ in the formula (1) or (2) is phenyl, thienyl, or a phenyl or thienyl group substituted with alkyl of 1–5 carbon atoms, alkoxy of 1–5 carbon atoms, halogen, or haloalkyl of 1–5 carbon atoms.

4. The alkylendiamine derivative as defined in claim 1, wherein R² in the formula (1) or (2) is phenyl, thienyl, or a phenyl or thienyl group substituted with alkyl of 1–5 carbon atoms, alkoxy of 1–5 carbon atoms, halogen, or haloalkyl of 1–5 carbon atoms.

5. The alkylenediamine derivative as defined in claim 1, wherein R³ and R⁴ are combined to form, in conjunction to nitrogen atom to which R³ and R⁴ are connected, morpholino, piperidino, homomorpholino, 1-pyrrolidyl, thiomorpholino, 1-piperazinyl, or morpholino substituted with alkyl of 1–5 carbon atoms.

6. A pharmaceutically acceptable salt of the alkylenediamine derivative defined in claim 1.

7. A method for the treatment of dysuria by administering to a patient in need thereof, a pharmaceutically effective amount of an alkylenediamine derivative or its pharmaceutically acceptable salt represented by the formula (1) or (2):

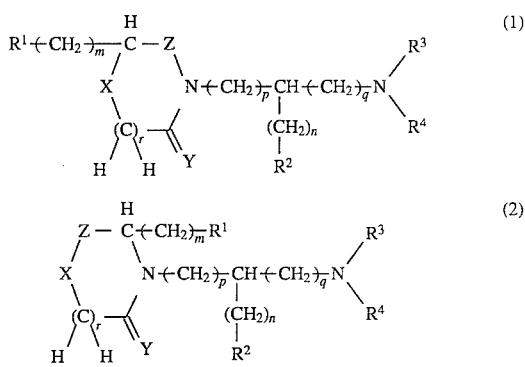

wherein

R¹ represents a hydrogen atom, an alkyl group, or a phenyl, naphthyl or aromatic heterocyclic group each of which is unsubstituted or substituted with the same or different 1 to 5 substituent groups selected from those consisting of alkyl groups, halogen atoms, haloalkyl groups, hydroxyl group, alkoxyl groups, aryloxy groups, aralkyloxy groups, nitro group, amino group, cyano group, alkylamino groups, aralkylamino groups, arylamino groups, acylamino groups, carboxyl group, alkoxycarbonyl groups, aralkyloxycarbonyl groups, aryloxycarbonyl groups, carbamoyl group, sulfo group, alkoxysulfonyl groups, aralkyloxysulfonyl groups, aryloxysulfonyl groups, sulfonamide group and 1H-tetrazol-5-yl group; R² represents a phenyl, naphthyl or aromatic heterocyclic group each of which may be unsubstituted or substituted with the same or different 1 to 5 substituent groups selected from those consisting of alkyl groups, halogen atoms, haloalkyl groups, hydroxyl group, alkoxyl groups, aryloxy groups, aralkyloxy groups, nitro group, amino group, cyano group, alkylamino groups, aralkylamino groups, arylamino groups, acylamino groups, carboxyl groups, alkoxy carbonyl groups, aralkyloxycarbonyl groups, aryloxycarbonyl groups, carbamoyl group, sulfo group, alkoxysulfonyl groups, aralkyloxysulfonyl groups, aryloxysulfonyl groups, sulfonamide group and 1H-tetrazol-5-yl group; each of R³ and R⁴ independently represents hydrogen atom, an alkyl group, an aralkyl group or an aryl group, or R³ and R⁴ are combined to form one of 5- to 7-membered cyclic groups which may contain oxygen atom, sulfur atom or nitrogen atom besides the nitrogen atom connected to both of R³ and R⁴ and which each of which may be unsubstituted or substituted with the same or different 1–5 substituent groups selected from those consisting of alkyl groups, aralkyl groups, phenyl group, hydroxyl group, alkoxyl groups, carboxyl group, alkoxycarbonyl groups, aralkyloxycarbonyl groups, aryloxycarbonyl groups, acyl groups and carbamoyl group; X represents oxygen atom, sulfur atom or imino group; Y represents oxygen atom or sulfur atom; Z represents —CH$_2$—, —CO— or —CS—; m is an integer of 0–4; n is an integer of 0–4; r is 0; and each of p and q independently represents an integer of 0–5 provide that p plus q is 1–5.

8. An alkylenediamine derivative represented by the formula (3):

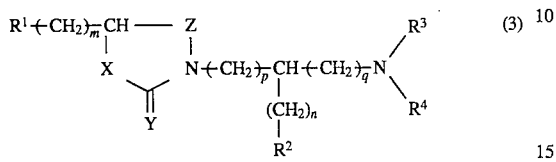

wherein
each of $R^1$ and $R^2$ independently represents a phenyl, naphthyl or aromatic heterocyclic group each of which is unsubstituted or substituted with the same or different 1 to 5 substituent groups selected from those consisting of alkyl groups, halogen atoms, haloalkyl groups, hydroxyl group, alkoxyl groups, aryloxy groups, aralkyloxy groups, nitro group, amino group, alkylamino groups, aralkylamino groups, arylamino groups, acylamino groups, carboxyl group, alkoxycarbonyl groups, aralkyloxycarbonyl groups, aryloxycarbonyl groups, carbamoyl group, sulfo group, alkoxysulfonyl groups, aralkyloxysulfonyl groups, aryloxysulfonyl groups, sulfonamide group and 1H-tetrazol-5-yl group; each of $R^3$ and $R^4$ independently represents hydrogen atom, an alkyl group, an aralkyl group or an aryl group, or $R^3$ and $R^4$ are combined to form one of 5- to 7-membered cyclic groups which may contain oxygen atom, sulfur atom or nitrogen atom besides the nitrogen atom connected to both of $R^3$ and $R^4$ and each of which is unsubstituted or substituted with the same or different 1 to 5 substituent groups selected from those consisting of alkyl groups, aralkyl groups, phenyl group, hydroxyl group, alkoxyl groups, carboxyl group, alkoxycarbonyl groups, aralkyloxycarbonyl groups, aryloxycarbonyl groups and carbamoyl group; X represents oxygen atom, sulfur atom or imino group; Y represents oxygen atom or sulfur atom; Z represents —CH$_2$—, —CO— or —CS—; m is an integer of 0–4; n is an integer of 0–4; and each of p and q independently represents an integer of 0–5 provided that p plus q is 1–5.

9. The alkylenediamine derivative as defined in claim 8, wherein X, Y and Z in the formula (3) represent oxygen atom, oxygen atom and —CH$_2$—, respectively.

10. The alkylenediamine derivative as defined in claim 8, wherein $R^1$ in the formula (3) is phenyl, thienyl, or a phenyl or thienyl group substituted with alkyl of 1–5 carbon atoms, alkoxy of 1–5 carbon atoms, halogen, or haloalkyl of 1–5 carbon atoms.

11. The alkylendiamine derivative as defined in claim 8, wherein $R^2$ in the formula (3) is phenyl, thienyl, or a phenyl or thienyl group substituted with alkyl of 1–5 carbon atoms, alkoxy of 1–5 carbon atoms, halogen, or haloalkyl of 1–5 carbon atoms.

12. The alkylenediamine derivative as defined in claim 8, wherein $R^3$ and $R^4$ are combined to form, in conjunction to nitrogen atom to which $R^3$ and $R^4$ are connected, morpholino, piperidino, homomorpholino, 1-pyrrolidyl, thiomorpholino, 1-piperazinyl, or morpholino substituted with alkyl of 1–5 carbon atoms.

13. A pharmaceutically acceptable salt of the alkylenediamine derivative defined in claim 8.

14. A method for treatment of dyuria by administering to a patient in need thereof, a pharmaceutically effective amount of the alkylenediamine derivative or its pharmaceutically acceptable salt defined in one of claims 8–13.

15. A method for treatment of dysuria by administering to a patient in need thereof, a pharmaceutically effective amount of the alkylenediamine derivative represented by the formula (1) or (2):

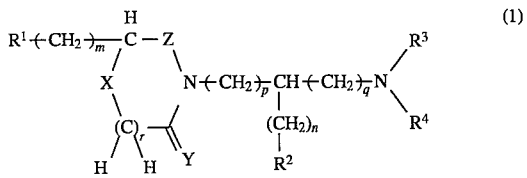

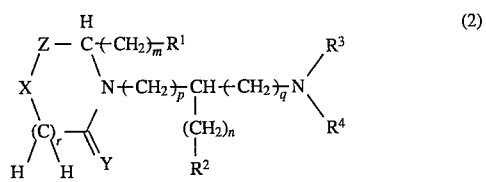

wherein
$R^1$ represents a hydrogen atom, an alkyl group, or a phenyl, naphthyl or aromatic heterocyclic group each of which is unsubstituted or substituted with the same or different 1 to 5 substituent groups selected from those consisting of alkyl groups, halogen atoms, haloalkyl groups, hydroxyl group, alkoxyl groups, aryloxy groups, aralkyloxy groups, nitro group, amino group, cyano group, alkylamino groups, aralkylamino groups, arylamino groups, acylamino groups, carboxyl group, alkoxycarbonyl groups, aralkyloxycarbonyl groups, aryloxycarbonyl groups, carbamoyl group, sulfo group, alkoxysulfonyl groups, arallcyloxysulfonyl groups, aryloxysulfonyl groups, sulfonamide group and 1H-tetrazol-5-yl group; $R^2$ represents a phenyl, naphthyl or aromatic heterocyclic group each of which is unsubstituted or substituted with the same or different 1 to 5 substituent groups selected from those consisting of alkyl groups, halogen atoms, haloalkyl groups, hydroxyl group, alkoxyl groups, aryloxy groups, aralkyloxy groups, nitro group, amino group, cyano group, alkylamino groups, aralkylamino groups, arylamino groups, acylamino groups, carboxyl group, alkoxy carbonyl groups, aralkyloxycarbonyl groups, aryloxycarbonyl groups, carbamoyl group, sulfo group, alkoxysulfonyl groups, aralkyloxysulfonyl groups, aryloxysulfonyl groups, sulfonamide group and 1H-tetrazol-5-yl group; each of $R^3$ and $R^4$ independently represents hydrogen atom, an alkyl group, an aralkyl group or an aryl group, or $R^3$ and $R^4$ are combined to form one of 5- to 7-membered cyclic groups which may contain oxygen atom, sulfur atom or nitrogen atom besides the nitrogen atom connected to both of $R^3$ and $R^4$ and each of which is unsubstituted or substituted with the same or different 1–5 substituent groups selected from those consisting of alkyl groups, aralkyl groups, phenyl group, hydroxyl group, alkoxyl groups, carboxyl group, alkoxycarbonyl groups, aralkyloxycarbonyl groups, aryloxycarbonyl groups, acyl groups and carbamoyl group; X represents oxygen atom, sulfur atom or imino group; Y represents oxygen atom or sulfur atom; Z represents —CH$_2$—, —CO— or —CS—; m is an integer of 0–4; n is an integer of 0–4; r is 0; and each of p and q independently represents an integer of 0–5 provide that p plus q is 1–5.

16. An alkylenediamine derivative represented by the formula (1) or (2):

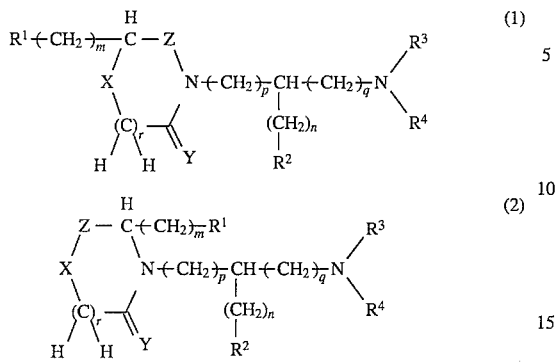

wherein

R$^1$ represents a hydrogen atom or an alkyl group R$^2$ represents a phenyl, naphthyl or aromatic heterocyclic group each of which is unsubstituted or substituted with the same or different 1 to 5 substituent groups selected from those consisting of alkyl groups, halogen atoms, haloalkyl groups, hydroxyl group, alkoxyl groups, aryloxy groups, aralkyloxy groups, nitro group, amino group, cyano group, alkylamino groups, aralkylamino groups, arylamino groups, acylamino groups, carboxyl group, alkoxycarbonyl groups, aralkyloxycarbonyl groups, aryloxycarbony groups, carbamoyl group, sulfo group, alkoxysulfonyl groups, aralkyloxysulfonyl groups, aryloxysulfonyl groups, sulfonamide group and 1H-tetrazol-5-yl group; R$^3$ and R$^4$ are combined to form one of 5- to 7-membered cyclic groups which may contain oxygen atom, sulfur atom or nitrogen atom besides the nitrogen atom connected to both of R$^3$ and R$^4$ and each of which is unsubstituted or substituted with the same or different 1 to 5 substituent groups selected from those consisting of alkyl groups, aralkyl groups, phenyl group, hydroxyl group, alkoxyl groups, carboxyl group, alkoxycarbonyl groups, aralkyloxycarbonyl groups, aryloxycarbonyl groups, acyl groups, and carbamoyl group; X represents oxygen atom, sulfur atom or imino group; Y represents oxygen atom or sulfur atom; Z represents —CH$_2$—, —CO— or —CS—; m is an integer of 0–4; n is an integer of 0–4; r is 0; and each of p and q independently represents an integer of 0–5 provided that p plus q is 1–5.

17. The alkylenediamine derivative as defined in claim 16, wherein R$^1$ in the formula (1) or (2) is phenyl, thienyl, or a phenyl or thienyl group substituted with alkyl of 1–5 carbon atoms, alkoxy of 1–5 carbon atoms, halogen, or haloalkyl of 1–5 carbon atoms.

18. The alkylendiamine derivative as defined in claim 16, wherein R$^2$ in the formula (1) or (2) is phenyl, thienyl, or a phenyl or thienyl group substituted with alkyl of 1–5 carbon atoms, alkoxy of 1–5 carbon atoms, halogen, or haloalkyl of 1–5 carbon atoms.

* * * * *